US008927757B2

(12) United States Patent
Ignatyev et al.

(10) Patent No.: US 8,927,757 B2
(45) Date of Patent: Jan. 6, 2015

(54) PROCESS FOR THE PREPARATION OF PERFLUOROALKYLCYANO- OR PERFLUOROALKYLCYANOFLUORO-BORATES

(75) Inventors: Nikolai (Mykola) Ignatyev, Duisburg (DE); Michael Schulte, Bischofsheim (DE); Jan Sprenger, Rommerskirchen (DE); Maik Finze, Nienburg (DE); Walter Frank, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 231 days.

(21) Appl. No.: 13/522,526

(22) PCT Filed: Jan. 12, 2011

(86) PCT No.: PCT/EP2011/000090
§ 371 (c)(1),
(2), (4) Date: Jul. 17, 2012

(87) PCT Pub. No.: WO2011/085966
PCT Pub. Date: Jul. 21, 2011

(65) Prior Publication Data
US 2012/0309981 A1    Dec. 6, 2012

(30) Foreign Application Priority Data
Jan. 18, 2010 (EP) .................................... 10000427

(51) Int. Cl.
*C07F 5/02* (2006.01)
*H01M 10/052* (2010.01)
*H01M 10/0568* (2010.01)
*H01G 9/20* (2006.01)

(52) U.S. Cl.
CPC .............. *C07F 5/02* (2013.01); *H01M 10/052* (2013.01); *H01M 10/0568* (2013.01); *H01G 9/2004* (2013.01); *H01G 9/2013* (2013.01); *H01G 9/2031* (2013.01); *H01G 9/2059* (2013.01); *Y02E 60/122* (2013.01)
USPC ...................................................... 558/384

(58) Field of Classification Search
CPC ...................................................... C07F 5/02
USPC ...................................................... 558/384
See application file for complete search history.

(56) References Cited

U.S. PATENT DOCUMENTS

| 7,208,626 | B2 | 4/2007 | Welz-Biermann et al. | |
|---|---|---|---|---|
| 7,632,969 | B2 | 12/2009 | Welz-Biermann et al. | |
| 7,645,434 | B2 | 1/2010 | Welz-Biermann et al. | |
| 8,686,285 | B2 | 4/2014 | Zhang et al. | |
| 2005/0119513 | A1 | 6/2005 | Ignatyev et al. | |
| 2007/0293391 | A1 | 12/2007 | Finze et al. | |
| 2011/0012048 | A1 | 1/2011 | Zhang et al. | |
| 2012/0309982 | A1* | 12/2012 | Shinohara et al. | 548/110 |
| 2014/0097376 | A1 | 4/2014 | Zhang et al. | |

FOREIGN PATENT DOCUMENTS

| CN | 101232080 A | 7/2008 |
|---|---|---|
| WO | WO-03 087020 | 10/2003 |
| WO | WO-03 087113 | 10/2003 |
| WO | WO-2004 072089 | 8/2004 |
| WO | WO-2006 045405 | 5/2006 |
| WO | WO-2008 102661 | 8/2008 |
| WO | 2009083901 A1 | 7/2009 |

OTHER PUBLICATIONS

Bernhardt, E. et al., "Synthesis and Properties of the Tetrakis(trifluoromethyl)borate Anion, [B(CF$_3$)$_4$]$^-$: Structure Determination of Cs[B(CF$_3$)$_4$] by Single-Crystal X-ray Diffraction," Chem. Eur. J., 2001, vol. 7, No. 21, pp. 4696-4705.
Bernhardt, E. et al., "The Reactions of M [BF$_4$] (M= Li, K) and (C$_2$H$_5$)$_2$O•BF$_3$ with (CH$_3$)$_3$SiCN. Formulations of M[BF$_x$(CN)$_{4-x}$] (M= Li, K; x=1, 2) and (CH$_3$)$_3$ SiNCBF$_x$ (CN)$_{3-x}$, (x= 0, 1)," Z. Anorg. Allg. Chem., 2003, vol. 629, pp. 677-685.
Chambers, R. D. et al., "Some salts of trifluoromethylfluoroboric acid$^{1,2}$," Journal of the American Chemical Society, 1960, vol. 82, pp. 5296-5301.
Frohn, H. J. et al., "A preparative method of perfluoroalkyltrifluoroborates and Perfluoroalkyldifluoroboranes," Z. Anorg. Allg. Chem., 2001, vol. 627, pp. 15-16.
International Search Report for PCT/EP2011/000090 dated Mar. 7, 2011.
Molander, G. A. et al., "Improved synthesis of Potassium (Trifluoromethyl)trifluoroborate [K(CF$^3$BF$^3$)]," Organometallics, 2003, vol. 22, pp. 3313-3315.
Rasmussen, J. K. et al., "The Chemistry of Cyanotrimethylsilane," Advances in Silicon Chemistry, 1991, vol. 1, pp. 65-187.
Reetz, M. T. et al., "An Improved Synthesis of Cyanotrimethylsilane," Synthesis, 1982, pp. 330.
Toyo Kasei Kogyo Co Ltd., "Method for producing trialkylsilylnitrile," Espacnet, Publication Date: Aug. 28, 2008; English Abstract of WO-2008 102661.
Wasserscheid, P. et al., "Ionic Liquids—New "Solution" for Transition Metal Catalysis," Angew. Chem. Int. Ed., 2000, vol. 39, pp. 3772-3789.
Zhou, Z. B. et al., "Novel electrolyte salts based on perfluoroalkyltrifluoroborate anions 1. Synthesis and characterization," Journal of Fluorine Chemistry, 2003, vol. 123, pp. 127-131.
Official Action dated May 23, 2014 related to corresponding Chinese Patent Application No. 201180006410.1.

* cited by examiner

*Primary Examiner* — Joseph Kosack
(74) *Attorney, Agent, or Firm* — Millen, White, Zelano & Branigan, P.C.

(57) ABSTRACT

The invention relates to a process for the preparation of salts having perfluoroalkyltricyano- or perfluoroalkylcyanofluoroborate anions, ((per)fluoro)phenyltricyano- or ((per)fluoro) phenylcyanofluoroborate anions, phenyltricyanoborate anions which are mono- or disubstituted by perfluoroalkyl groups having 1 to 4C atoms or phenylcyanofluoroborate anions which are mono- or disubstituted by perfluoroalkyl groups having 1 to 4C atoms, by reaction of alkali metal trifluoroperfluoroalkylborate with trialkylsilyl cyanide and a subsequent salt-exchange reaction or by direct reaction of an organic trifluoroperfluoroalkyl borate with trialkylsilyl cyanide.

9 Claims, No Drawings

PROCESS FOR THE PREPARATION OF PERFLUOROALKYLCYANO- OR PERFLUOROALKYLCYANOFLUORO-BORATES

The invention relates to a process for the preparation of salts having perfluoroalkyltricyano- or perfluoroalkylcyanofluoroborate anions, ((per)fluoro)-phenyltricyano- or ((per)fluoro)phenylcyanofluoroborate anions, phenyltricyanoborate anions which are mono- or disubstituted by perfluoroalkyl groups having 1 to 4 C atoms or phenylcyanofluoroborate anions which are mono- or disubstituted by perfluoroalkyl groups having 1 to 4 C atoms, by reaction of alkali metal trifluoroperfluoroalkylborate with trialkylsilyl cyanide and a subsequent salt-exchange reaction or by direct reaction of an organic trifluoroperfluoroalkyl borate with trialkylsilyl cyanide.

Salts of the formula $M^{a+}[B(R_f)_{4-x-y}(CN)_x(F)_y]_a^-$, where $M^{a+}$ can be an inorganic or organic cation and a=1 or 2, x=1, 2 or 3, y=0 or 1 and x+y≤4, are known from WO 2006/045405, where, however, only the salts potassium tris(trifluoromethyl)cyanoborate, guanidinium tris(trifluoromethyl)-cyanoborate and tritylium tris(trifluoromethyl)cyanoborate are disclosed. WO 2006/045405 describes that salts having organic cations and anions of the formula indicated are ionic liquids.

An ionic liquid is taken to mean salts which generally consist of an organic cation and an inorganic anion. They do not contain any neutral molecules and usually have melting points below 373 K [Wasserscheid P, Keim W, 2000, *Angew. Chem.* 112: 3926]. Due to their salt character, ionic liquids have unique substance properties, such as, for example, a low vapour pressure, a liquid state over a broad temperature range, are non-flammable, exhibit high electrical conductivity and high electrochemical and thermal stability.

Surprisingly, ionic liquids having a borate anion which contain both perfluoroalkyl and also cyano groups exhibit a lower viscosity than ionic liquids having borate anions which contain perfluoroalkyl groups and fluoro groups, such as, for example, perfluoroalkyl trifluoroborate, or lower viscosity than ionic liquids having tetracyanoborate anions. The viscosity is an important substance property if applications of the salts having perfluoroalkylcyanofluoroborate anions are considered, in particular in electrochemistry. In particular, salts having the anions perfluoroalkyltricyanoborate, perfluoroalkylcyanodifluoroborate or perfluoroalkyldicyanofluoroborate exhibit dynamic viscosities, for example, in the order of 13 to 17 cP at 25° C. Salts of this type having these selected anions are novel, and in particular a selection invention of WO 2006/045405.

The synthesis of the borate anions $[B(R_f)_{4-x-y}(CN)_x(F)_y]$ where x=1, 2 or 3, y=0 or 1 and x+y<4 succeeds, according to the description of the published specification WO 2006/045405, by isomerisation of the corresponding isocyanoborate salts at temperatures between 150° and 300° C. The isocyanoborate salts form by reaction of isocyanoboric acid with a strong base and are characterised in that the nitrogen atom is bonded to the boron atom. By comparison, the cyanide in the salts of WO 2006/045405 is bonded to the boron atom via the C atom.

E. Bernhard et al, Chemistry A European J. 2001, 7, No. 21, 4696-4705) describes NMR data of the anions $[(CF_3)BF_2(CN)]^-$ and $[(CF_3)BF(CN)_2]^-$, which were observed during the fluorination of lithium, silver or ammonium tetracyanoborate ($NH_4[B(CN)_4]$) using $ClF_3$, but were not isolated. The end product of this fluorination are salts having a tetratrifluoromethylborate anion ($[B(CF_3)_4]^-$).

The synthesis of alkali metal tetracyanoborates by a solid-state reaction of an alkali metal tetrafluoroborate in the presence of potassium cyanide/lithium chloride is described, for example, in WO 2004/072089.

The synthesis of borate anions without a perfluoroalkyl group $[B(CN)_x(F)_y]$ where x=2 or 3, y=1 or 2 and x+y=4 succeeds, according to the description of E. Bernhard et al, Z. für Anorg. Allg. Chem. 2003, 629, 677-685, by reaction of lithium tetrafluoroborate or potassium tetrafluoroborate with trimethylsilyl cyanide. It is furthermore described in this reference that the reaction rate is very slow, the reaction time is several hours to several weeks and that mixtures of dicyanodifluoroborate anions and tricyanofluoroborate anions generally form. The synthesis and isolation of trifluoromonocyanoborate anions was not possible by this method.

However, there continues to be a demand for economical alternative synthetic methods for the preparation of this interesting class of salts having perfluoroalkylcyanofluoroborate anions or perfluoroalkyltricyanoborate anions, perfluorophenylcyanofluoroborate anions or perfluorophenyltricyanoborate anions, fluorophenylcyanofluoroborate anions or fluorophenyltricyanoborate anions, phenylcyanofluoroborate anions or phenyltricyanoborate anions, which may optionally be mono- or disubstituted by perfluoroalkyl groups having 1 to 4 C atoms.

The object of the present invention is therefore to develop an alternative preparation process which gives the desired salts in good yield and starts from readily accessible starting materials.

Surprisingly, it has been found that alkali metal trifluoroperfluoroalkylborates represent excellent starting materials for the synthesis of the desired mixed borates, which are readily accessible.

The invention therefore relates to a process for the preparation of salts of the formula I

$$M^{a+}[B(R_f)(CN)_x(F)_y]_a^- \qquad \text{I,}$$

where
$M^{a+}$ is a silver, magnesium, copper(I), copper(II), zinc(II), calcium cation, $NH_4^+$ or an organic cation,
$R_f$ denotes a linear or branched perfluorinated alkyl group having 1 to 4 C atoms, $C_6F_5$, $C_6H_5$, partially fluorinated phenyl, or phenyl which is mono- or disubstituted by a perfluoroalkyl group having 1 to 4 C atoms, where the perfluoroalkyl group is selected independently of one another,
a is 1 or 2,
x is 1, 2 or 3,
y is 0, 1 or 2 and
x+y=3,
by reaction of an alkali metal salt of the formula II

$$Me^+[B(R_f)F_3]^- \qquad \text{II,}$$

where
$Me^+$ is a lithium, potassium, sodium, caesium or rubidium salt and $R_f$ has a meaning indicated above
with trialkylsilyl cyanide to give a salt of the formula III

$$Me^+[B(R_f)(CN)_x(F)_y]^- \qquad \text{III,}$$

where $Me^+$, $R_1$, x and y have a meaning indicated above and the alkyl group of the trialkylsilyl cyanide is in each case, independently of one another, a linear or branched alkyl group having 1 to 4 C atoms,
and by the subsequent salt-exchange reaction of the salts of the formula III with a salt of the formula IV,

$$MA \qquad \text{IV,}$$

where
M has a meaning indicated for $M^{a+}$ and
A is selected from the group of the anions F⁻, Cl⁻, Br⁻, I⁻, OH⁻, [HF₂]⁻, [CN]⁻, [SCN]⁻, [R₁COO]⁻, [R₁SO₃]⁻, [R₂COO]⁻, [R₂SO₃]⁻, [R₁OSO₃]⁻, [SiF₆]²⁻, [BF₄]⁻, [SO₄]²⁻, [HSO₄]¹⁻, [NO₃]⁻, [(R₁)₂P(O)O]⁻, [R₁P(O)O₂]²⁻, [(R₁O)₂P(O)O]⁻, [(R₁O)P(O)O₂]²⁻, [(R₂)₂P(O)O]⁻, [R₂P(O)O₂]²⁻, tosylate, benzoate, oxalate, succinate, suberate, ascorbate, sorbate, tartrate, citrate, malate, malonate, malonates which are optionally substituted by alkyl groups having 1 to 4 C atoms, or [CO₃]²⁻, where R₁ in each case, independently of one another, denotes H and/or a linear or branched alkyl group having 1 to 12 C atoms, R₂ in each case, independently of one another, denotes a partially fluorinated or perfluorinated linear or branched alkyl group having 1 to 12 C atoms or pentafluorophenyl and where electroneutrality must be ensured in the formula of the salt MA.

A perfluorinated linear or branched alkyl group having 1 to 4 C atoms is, for example, trifluoromethyl, pentafluoroethyl, n-heptafluoropropyl, isoheptafluoropropyl, n-nonafluorobutyl, sec-nonafluorobutyl or tert-nonafluorobutyl. R₂ defines analogously a linear or branched perfluorinated alkyl group having 1 to 12 C atoms, containing the above-mentioned perfluoroalkyl groups and, for example, perfluorinated n-hexyl, perfluorinated n-heptyl, perfluorinated n-octyl, perfluorinated ethylhexyl, perfluorinated n-nonyl, perfluorinated n-decyl, perfluorinated n-undecyl or perfluorinated n-dodecyl.

$R_f$ is preferably trifluoromethyl, pentafluoroethyl, heptafluoropropyl, nonafluorobutyl, perfluorohexyl, C₆F₅, p-FC₆H₄, 3,5-(CF₃)₂C₆H₃ or C₆H₅; particularly preferably a linear or branched perfluorinated alkyl group having 1 to 4 C atoms or C₆F₅, very particularly preferably trifluoromethyl or pentafluoroethyl, extraordinarily preferably pentafluoroethyl.

Accordingly, preferred salts of the formula I in which the borate anions are selected from the group trifluoromethyltricyanoborate, pentafluoroethyltricyanoborate, heptafluoropropyltricyanoborate, trifluoromethyldicyanofluoroborate, pentafluoroethyldicyanofluoroborate, heptafluoropropyldicyanofluoroborate, trifluoromethylmonocyanodifluoroborate, pentafluoromethylmonocyanodifluoroborate, heptafluoropropylmonocyanodifluoroborate, nonafluorobutylmonocyanodifluoroborate, pentafluorophenyltricyanoborate, pentafluorophenyldicyanofluoroborate, pentafluorophenylmonocyanodifluoroborate, phenyltricyanoborate, phenyldicyanofluoroborate, phenylmonocyanodifluoroborate, p-fluorophenyltricyanoborate, p-fluorophenyldicyanofluoroborate, p-fluorophenylmonocyanodifluoroborate, 3,5-bis(trifluoromethyl)phenyltricyanoborate, 3,5-bis(trifluoromethyl)-phenyldicyanofluoroborate or 3,5-bis(trifluoromethyl)phenylmonocyanodifluoroborate.

R₂ is particularly preferably trifluoromethyl, pentafluoroethyl or nonafluorobutyl, very particularly preferably trifluoromethyl or pentafluoroethyl.

A linear or branched alkyl group having 1 to 4 C atoms is, for example, methyl, ethyl, n-propyl, isopropyl, n-butyl, sec-butyl or tert-butyl. R₁ defines analogously a linear or branched alkyl group having 1 to 12 C atoms, containing the above-mentioned alkyl groups and, for example, n-hexyl, n-heptyl, n-octyl, ethylhexyl, n-nonyl, n-decyl, n-undecyl or n-dodecyl.

R₁ is particularly preferably methyl, ethyl, n-butyl, n-hexyl or n-octyl, very particularly preferably methyl or ethyl.

Substituted malonates are, for example, the compounds— methyl malonate or ethyl malonate.

$M^{a+}$ is preferably an organic cation selected from ammonium cations, sulfonium cations, oxonium cations, phosphonium cations, uronium cations, thiouronium cations, guanidinium cations or heterocyclic cations, as described below, in particular by the formulae (1) to (8), and preferred meanings thereof.

The alkyl groups of the trialkylsilyl cyanide may be identical or different. The alkyl groups are preferably identical. Examples of trialkylsilyl cyanides are therefore trimethylsilyl cyanide, triethylsilyl cyanide, triisopropylsilyl cyanide, tripropylsilyl cyanide or tributylsilyl cyanide. Particular preference is given to the use of trimethylsilyl cyanide, which is commercially available or can also be prepared in situ.

Preference is given to the use of compounds of the formula II in which the alkali metal is lithium, sodium or potassium, particularly preferably potassium.

Very particularly preferred compounds of the formula II for the synthesis of the compounds of the formula I, as described above, are therefore to be selected from potassium trifluoromethyltrifluoroborate, potassium pentafluoroethyltrifluoroborate, potassium heptafluoropropyltrifluoroborate or potassium pentafluorophenyltrifluoroborate.

It is now possible to select the reaction conditions of this reaction in such a way that, in particular in the case of the conversion of the compounds of the formula II into compounds of the formula III, as described above, a specific borate anion is obtained specifically in high yield. Without specific temperature control, a mixture of salts having different borate anions, as defined above or as described as preferred, generally form. The temperature control is advantageously through microwave irradiation.

Compounds of the formula II can be prepared by conventional methods known to the person skilled in the art, for example based on the description in U.S. Pat. No. 7,208,626 B2; WO 2003/087020 (A1) and WO 2003/087113 (A1) or in R. D. Chambers et al., *J. of the American Chemical Society*, 82 (1960), p. 5296-5301; H.-J-Frohn and V. V. Bardin, *Z. für Anorganische and Allgemeine Chemie*, 627 (2001), pp. 15-16; G. A. Molander and G. P. Hoag, *Organometallics*, 22 (2003), p. 3313-3315; Zhi-Bin Zhou et al., *J. of Fluorine Chem.*, 123 (2003), p. 127-131].

If the reaction of the compound of the formula II

Me⁺[B(R_f)F₃]⁻                II, where

Me⁺ is a lithium, potassium, sodium, caesium or rubidium salt and R_f has a meaning indicated above
with trialkylsilyl cyanide is carried out, as described above, at temperatures between 10° C. and 110° C. or with microwave irradiation with 100 W, compounds of the formula III

Me⁺[B(R_f)(CN)_x(F)_y]⁻                III, where Me⁺, R_f, have the meaning as for the compound of the formula II and x=1 and y=2, i.e. a fluorine atom is replaced by a cyano group, form in particular. Compounds of the formula III having an anion of the formula Ia

[B(R_f)(CN)(F)₂]⁻                Ia, thus form in high yield.

If the group R_f denotes trifluoromethyl, the corresponding salt having the trifluoromethylmonocyanodifluoroborate anion preferably forms at room temperature or on microwave irradiation with 100 W. A reaction time of several hours can be observed. The details in this respect are described in the examples. If the group R_f denotes pentafluoroethyl, the corresponding salt preferably forms at temperatures of 100° C. with a reaction time in the order of one hour or on microwave irradiation with 100 W. If the group R_f denotes phenyl, partially fluorinated phenyl, phenyl or perfluorophenyl, each of which is mono- or disubstituted by perfluoroalkyl groups having 1 to 4 C atoms, the corresponding monocyanodifluoroborate salt preferably forms at room temperature with a reaction time of several days. A preferred embodiment for the preparation of salts of the formula I having anions of the formula Ia is therefore characterised in that the reaction of the formula II with the trialkylsilyl cyanide, as described above, is carried out at temperatures between 10° C. and 110° C., preferably between room temperature (25° C.) and 100° C., or with microwave irradiation with 100 W.

If the reaction of the compound of the formula II $$Me^+[B(R_f)F_3]^- \qquad II,$$

where

Me$^+$ is a lithium, potassium, sodium, caesium or rubidium salt and R$_f$ has a meaning indicated above
with trialkylsilyl cyanide is carried out, as described above, at temperatures between 115° C. and 200° C. or with microwave irradiation with 200 W, compounds of the formula III $$Me^+[B(R_f)(CN)_x(F)_y]^- \qquad III,$$

where Me$^+$, R$_f$ have the meaning as for the compound of the formula II and x=2 and y=1, i.e. two fluorine atoms are replaced by cyano groups, form in particular. Compounds of the formula III having an anion of the formula Ib $$[B(R_f)(CN)_2(F)]^- \qquad Ib,$$

thus form in high yield.

If the group R$_f$ denotes, for example, trifluoromethyl, the corresponding salt having the trifluoromethyldicyanofluoroborate anion preferably forms at 130° C. or with microwave irradiation with 200 W. The reaction time is in the order of 5 hours. The details in this respect are described in the examples. If the group R$_f$ denotes, for example, pentafluoroethyl, the corresponding salt of the formula Ib preferably forms at temperatures of 180° C. with a reaction time in the order of 6 hours or with microwave irradiation with 200 W with a reaction time in the order of several minutes. A preferred embodiment for the preparation of salts of the formula I having anions of the formula Ib is therefore characterised in that the reaction of the formula II with the trialkylsilyl cyanide, as described above, is carried out at temperatures between 115° C. and 200° C., preferably between 130° C. and 180° C., or with microwave irradiation with 200 W.

If the reaction of the compound of the formula II $$Me^+[B(R_f)F_3]^- \qquad II,$$

where

Me$^+$ is a lithium, potassium, sodium, caesium or rubidium salt and R$_f$ has a meaning indicated above
with trialkylsilyl cyanide is carried out, as described above, with microwave irradiation with greater than 200 W, in particular with 300 W, compounds of the formula III $$Me^+[B(R_f)(CN)_x(F)_y]^- \qquad III,$$

where Me$^+$ and R$_f$ have the meaning as for the compound of the formula II and x=3 and y=0, i.e. all three fluorine atoms are replaced by cyano groups, form in particular. Compounds of the formula III having an anion of the formula Ic $$[B(R_f)(CN)_3]^- \qquad Ic,$$

thus form in high yield.

A preferred embodiment for the preparation of salts of the formula I having anions of the formula Ic is therefore characterised in that the reaction of the formula II with the trialkylsilyl cyanide is carried out as described above with microwave irradiation greater than 200 W, preferably with microwave irradiation with 300 W.

If the group R$_f$ denotes, for example, trifluoromethyl, the corresponding salt having the trifluoromethyltricyanofluoroborate anion preferably forms on microwave irradiation with 300 W. The reaction time is in the order of one to two hours. The details in this respect are described in the examples. If the group R$_f$ denotes, for example, pentafluoroethyl, the corresponding salt is preferably forms with microwave irradiation with 300 W with a reaction time in the order of one hour.

It was not foreseeable that the compounds of the formula II, as described above, are suitable as starting materials for the preparation of the compounds of the formula III and, after salt-exchange reaction, for the preparation of compounds of the formula I. In contrast to the reaction described in Bernhard et al (Z. für Anorg. Allg. Chem. 2003, 629, 677-685) of an alkali metal tetrafluoroborate with trimethylsilyl cyanide, it cannot be expected that the reactivity in the presence of the bulky group R$_f$, for example in the presence of a perfluoroalkyl group, is sufficient to facilitate replacement of fluorine atoms by cyano groups. It is furthermore surprising that the reaction rate even increases in relation. The replacement of three fluorine atoms did not succeed in the reference mentioned above, whereas precisely such a replacement occurs in the process according to the invention in the presence of microwave radiation with 300 W. Microwave irradiation as heating source is not described in the reference. Unexpectedly and surprisingly, trimethylsilyl cyanide attacks selectively only the fluorine atoms bonded to boron, but not the fluorine atoms in the perfluoroalkyl chain. The reaction of the compounds of the formula II with the trialkylsilyl cyanide can be carried out without protective-gas atmosphere. However, the reaction is preferably carried out under dried air or in an inert-gas atmosphere. The reaction of the compounds of the formula II with the trialkylsilyl cyanide is preferably carried out without solvents. However, the reaction in the presence of an organic solvent, for example tetrahydrofuran or acetonitrile, is possible.

In a further embodiment, the trialkylsilyl cyanide used is prepared in situ from an alkali metal cyanide and a trialkylsilyl chloride in the presence of an alkali metal iodide or fluoride and optionally iodine before the reaction with a compound of the formula II, as described above. Use is preferably made here of sodium cyanide and sodium iodide or potassium cyanide and potassium iodide, where the alkali metal iodide is preferably added in a molar amount of 0.1 mol/l based on 1 mol/l of alkali metal cyanide and trialkylsilyl chloride. Details on this preparation are given in the examples. In general, this process for the preparation is based on the description of M. T. Reetz, I. Chatziiosifidis, Synthesis, 1982, p. 330; J. K. Rasmussen, S. M. Heilmann and L. R. Krepski, The Chemistry of Cyanotrimethylsilane in G. L. Larson (Ed.) "Advances in Silicon Chemistry", Vol. 1, p. 65-187, JAI Press Inc., 1991 or WO 2008/102661 A1.

The invention therefore also relates to a process for the preparation of compounds of the formula I, as described above, characterised in that the trialkylsilyl cyanide is prepared in situ from an alkali metal cyanide and a trialkylsilyl chloride in the presence or catalysis of an alkali metal iodide and optionally iodine before the reaction with a compound of the formula II.

If the preparation according to the invention of compounds of the formula I is carried out as described above, it is possible to purify the compounds of the formula III obtained from the first step of the reaction and to employ them as isolated, pure compound in the second step of the salt-exchange reaction or metathesis reaction.

However, it is advantageous in a further embodiment not to work up the intermediate compound of the formula III to give the pure substance, but instead merely to separate off the by-products which are insoluble in organic solvents or are readily volatile, such as, for example, trialkylsilyl fluoride or an excess of trimethylsilyl cyanide, and to react the compound of the formula III without further purification to give the pure substance with a compound of the formula IV, as described above.

Alternatively, the synthesis of the compounds of the formula I, as described above, can also be carried out by reaction of a compound of the formula II, as described above, with an alkali metal cyanide in the presence of an alkali metal chloride, as described, for example, in Example 5C. The compounds obtained can be separated by crystallisation. If the mixture is used for the preparation of compounds having corresponding organic cations in a salt-exchange reaction, the salts having organic cations can be separated, for example, via extraction methods. This alternative process is preferably suitable for the preparation of alkali metal (pentafluoroethyl) difluoromonocyanoborates and the corresponding organic salts or alternative metal salts after salt exchange. A preferred alkali metal chloride is lithium chloride. This is a sinter reaction, in particular at temperatures between 160° C. and 200° C.

Examples of organic cations of the formulae (1) to (8) can be selected from the group:
ammonium cations of the formula (1), sulfonium cations of the formula (2) or oxonium cations of the formula (3)

  (1),

  (2) or

  (3)

where
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or two R may be fully substituted and/or one or more R may be partially substituted by halogens or partially by $-OR^1$, $-NR^{1+}_2$, $-CN$, $-C(O)NR^1_2$ or $-SO_2NR^1_2$,
and where one or two non-adjacent carbon atoms which are not in the α-position of the radical R may be replaced by atoms and/or atom groups selected from the group $-O-$, $-S-$, $-S(O)-$, $-SO_2-$, $-N^+R^1_2-$, $-C(O)NR^1-$, $-SO_2NR^1-$ or $-P(O)R^1-$; or
phosphonium cations of the formula (4)

  (4), where
$R^2$ in each case, independently of one another, denotes
H, $NR^{1*}_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or two $R^2$ may be fully substituted and/or one or more $R^2$ may be partially substituted by halogens, or partially by $-OR^1$, $-CN$, $-C(O)NR^1_2$, $-SO_2NR^1_2$,
and where one or two non-adjacent carbon atoms which are not in the α-position of the $R^2$ may be replaced by atoms and/or atom groups selected from the group $-O-$, $-S-$, $-S(O)-$, $-SO_2-$, $-N^+R^1_2-$, $-C(O)NR^1-$, $-SO_2NR^1-$, or $-P(O)R^1-$; or
uronium cations of the formula (5) or thiouronium cations of the formula (6)

  (5)

or

  (6), where
$R^3$ to $R^7$ each, independently of one another, denote
H, $NR^{1*}_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents $R^3$ to $R^7$ may be partially or fully substituted by halogens, or partially by $-OH$, $-OR^1$, $-CN$, $-C(O)NR^1_2$, $-SO_2NR^1_2$,
and where one or two non-adjacent carbon atoms which are not in the α-position of $R^3$ to $R^7$ may be replaced by atoms and/or atom groups selected from the group $-O-$, $-S-$, $-S(O)-$, $-SO_2-$, $-N^+R^1_2-$, $-C(O)NR^1-$, $-SO_2NR^1-$, or $-P(O)R^1-$; or
guanidinium cations of the formula (7)

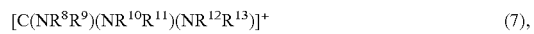  (7), where
$R^8$ to $R^{13}$ each, independently of one another, denote $-H$, $NR^{1*}_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents $R^8$ to $R^{13}$ may be partially or fully substituted by halogens or partially by $-OR^1$, $-CN$, $-C(O)NR^1_2$, $-SO_2NR^1_2$,
and where one or two non-adjacent carbon atoms which are not in the α-position of $R^8$ to $R^{13}$ may be replaced by atoms and/or atom groups selected from the group $-O-$, $-S-$, $-S(O)-$, $-SO_2-$, $-N^+R^1_2-$, $-C(O)NR^1-$, $-SO_2NR^1-$, or $-P(O)R^1-$; or
heterocyclic cations of the formula (8)

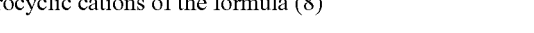  (8), where $[HetN]^+$ is a heterocyclic cation, selected from the group comprising

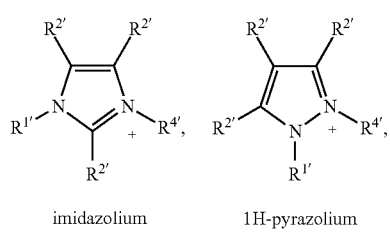

imidazolium     1H-pyrazolium

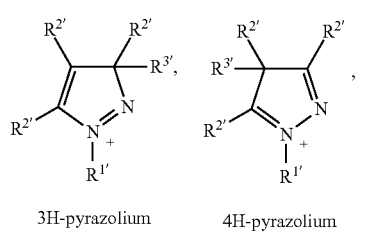

3H-pyrazolium     4H-pyrazolium

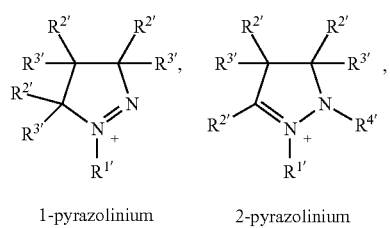

1-pyrazolinium     2-pyrazolinium

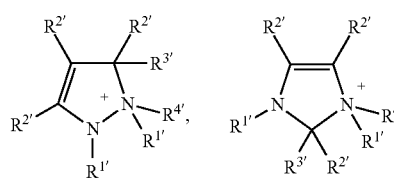

3-pyrazolinium     2,3-dihydroimidazolinium

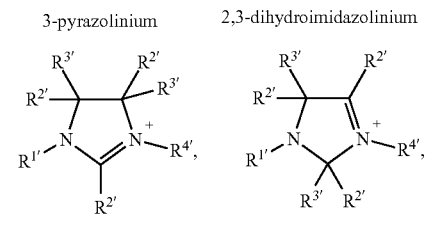

4,5-dihydroimidazolinium     2,5-dihydroimidazolinium

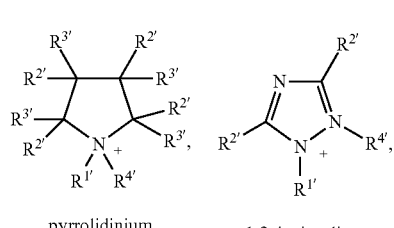

pyrrolidinium     1,2,4-triazolium

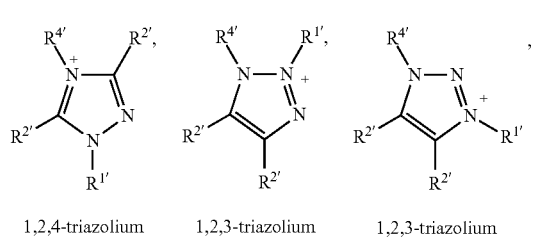

1,2,4-triazolium     1,2,3-triazolium     1,2,3-triazolium

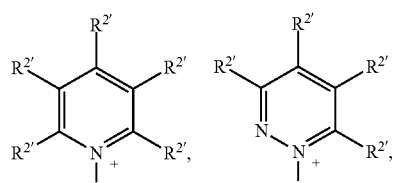

pyridinium     pyridazinium

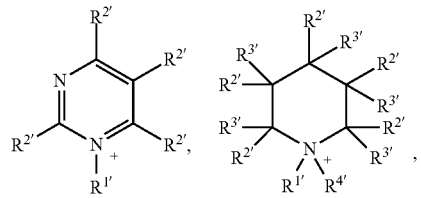

pyrimidinium     piperidinium

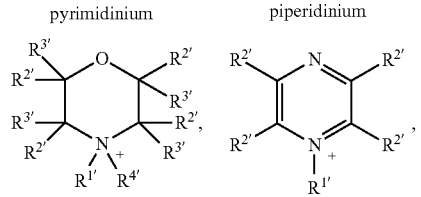

morpholinium     pyrazinium

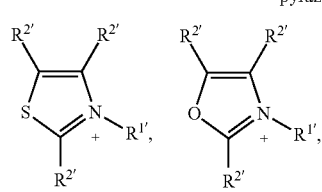

thiazolium     oxazolium

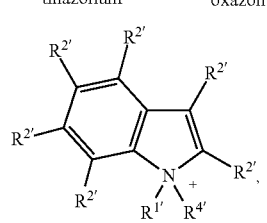

indolium

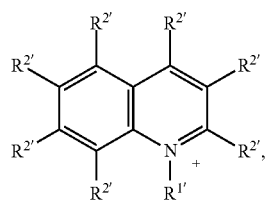

quinolinium

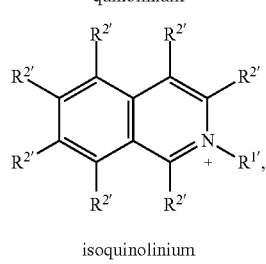

isoquinolinium

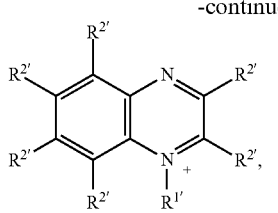

quinoxalinium

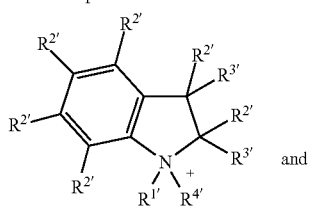

and indolinium

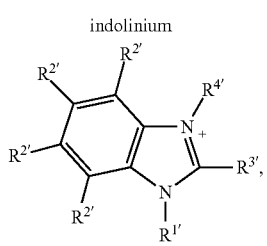

benzimidazolium where the substituents $R^{1'}$ to $R^{4'}$ each, independently of one another, denote
- H, with the restriction that $R^{1'}$ and $R^{4'}$ cannot simultaneously be H,
- straight-chain or branched alkyl having 1-20 C atoms, which may also be fluorinated or perfluorinated,
- straight-chain or branched alkenyl having 2-20 C atoms and one or more double bonds, which may also be fluorinated or perfluorinated,
- straight-chain or branched alkynyl having 2-20 C atoms and one or more triple bonds, which may also be fluorinated or perfluorinated,
- saturated, partially or fully unsaturated cycloalkyl having 3-7 C atoms, which may be substituted by alkyl groups having 1-6 C atoms,
- saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may form a ring system,
where one or more substituents $R^{1'}$ to $R^{4'}$ may be partially or fully substituted by halogens or partially by —$OR^1$, —CN, —C(O)$NR^1_2$, —$SO_2NR^1_2$, but where $R^{1'}$ and $R^{4'}$ cannot simultaneously be fully substituted by halogens, and where one or two non-adjacent carbon atoms which are not bonded to the heteroatom of the substituents $R^{1'}$ to $R^{4'}$ may be replaced by atoms and/or atom groups selected from the group —O—, —S—, —S(O)—, —$SO_2$—, —$N^+R^1_2$—, —C(O)$NR^1$—, —$SO_2NR^1$—, or —P(O)$R^{1*}$—;
in which $R^1$ stands for H, non-, partially or perfluorinated $C_1$- to $C_6$-alkyl, $C_3$- to $C_7$-cycloalkyl, unsubstituted or substituted phenyl and $R^{1*}$ stands for non-, partially or perfluorinated $C_1$- to $C_6$-alkyl, $C_3$- to $C_7$-cycloalkyl, unsubstituted or substituted phenyl.

Cations of the formulae (1), (2), (3) and (4) in which all four or three substituents R and $R^2$ are fully substituted by halogens, for example the tris-(trifluoromethyl)methylammonium cation, the tetrakis(trifluoromethyl)-ammonium cation or the tetrakis(nonafluorobutyl)ammonium cation, are therefore excluded.

Fully unsaturated substituents in the sense of the present invention are also taken to mean aromatic substituents.

Suitable substituents R and $R^2$ to $R^{13}$ of the compounds of the formulae (1) to (7) in accordance with the invention are, besides H, preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (1), (2), (3) or (4) may be identical or different here. In compounds of the formulae (1), three or four substituents R are preferably identical. In compounds of the formulae (2), all substituents R are preferably identical or two are identical and one substituent is different. In compounds of the formula (3), all substituents R are preferably identical. In compounds of the formula (3), three or four substituents $R^2$ are preferably identical.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation $[C(NR^8R^9)(NR^{10}R^{11})\text{—}(NR^{12}R^{13})]^+$ may also be connected in pairs in such a way that mono-, bi- or polycyclic molecules form.

Without restricting generality, examples of guanidinium cations of this type are:

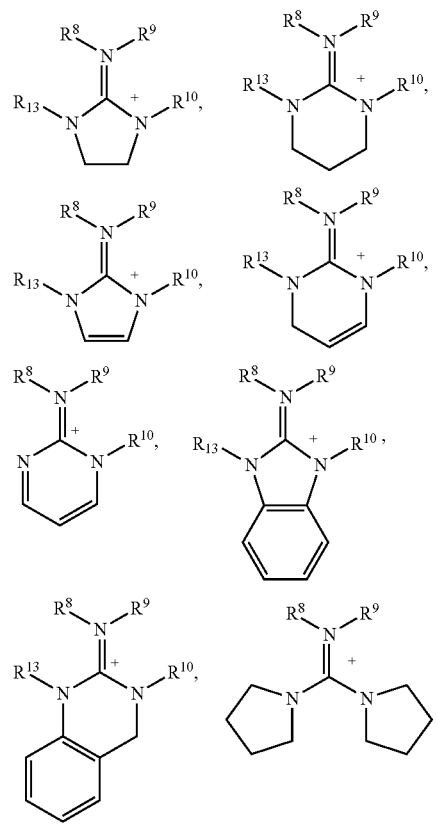

-continued

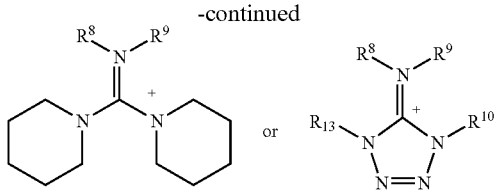

where the substituents $R^8$ to $R^{10}$ and $R^{13}$ may have an above-mentioned or particularly preferred meaning.

The carbocycles or heterocycles of the above-mentioned guanidinium cations may optionally also be substituted by $C_1$- to $C_6$-alkyl, $C_1$- to $C_6$-alkenyl, CN, $NR^1{}_2$, F, Cl, Br, I, $C_1$-$C_6$-alkoxy, $SCF_3$, $SO_2CF_3$ or $SO_2NR^1{}_2$, where $R^1$ has an above-mentioned meaning, substituted or unsubstituted phenyl or an unsubstituted or substituted heterocycle.

Up to four substituents of the thiouronium cation $[C(NR^3R^4)(SR^5)(NR^6R^7)]^+$ may also be connected in pairs in such a way that mono-, bi- or polycyclic molecules arise.

Without restricting generality, examples of thiouronium cations of this type are indicated below:

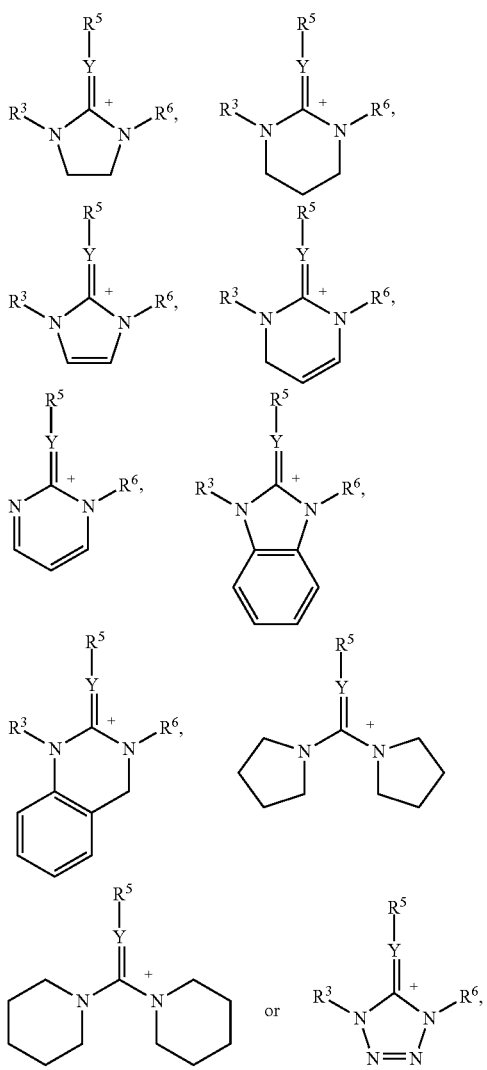

in which Y=S
and where the substituents $R^3$, $R^5$ and $R^6$ may have an above-mentioned or particularly preferred meaning.

The carbocycles or heterocycles of the above-mentioned molecules may optionally also be substituted by $C_1$- to $C_6$-alkyl, $C_1$- to $C_6$-alkenyl, CN, $NR^1{}_2$, F, Cl, Br, I, $C_1$-$C_6$-alkoxy, $SCF_3$, $SO_2CF_3$ or $SO_2NR^1{}_2$ or substituted or unsubstituted phenyl or an unsubstituted or substituted heterocycle, where $R^1$ has an above-mentioned meaning.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (5) to (7) may be identical or different here. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

Suitable substituents $R^{1'}$ to $R^{4'}$ of compounds of the formula (8) in accordance with the invention are, besides H, preferably: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, pentyl, hexyl, octyl, decyl, cyclohexyl, phenyl or benzyl. They are very particularly preferably methyl, ethyl, n-butyl or hexyl. In pyrrolidine, piperidine, indoline, pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally difluoromethyl, trifluoromethyl, pentafluoroethyl, heptafluoropropyl or nonafluorobutyl.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, preference is furthermore given to 4-pentenyl, isopentenyl or hexenyl. If the compounds are partially fluorinated, at least one H atom is replaced by an F atom. If the compounds are perfluorinated, all H atoms of the corresponding alkyl group have been replaced by F atoms.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl. If the compounds are partially fluorinated, at least one H atom is replaced by an F atom. If the compounds are perfluorinated, all H atoms of the corresponding alkyl group have been replaced by F atoms.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OR$^1$, —NR$^1_2$, —CN, —C(O)NR$^1_2$, —SO$_2$NR$^1_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclohexenyl, phenyl, cycloheptenyl, each of which may be substituted by $C_1$- to $C_6$-alkyl groups, where the cycloalkyl group or the cycloalkyl group which is substituted by $C_1$- to $C_6$-alkyl groups may in turn also be substituted by halogen atoms, such as F, Cl, Br or I, in particular F or Cl, or by —OR$^1$, —CN, —C(O)NR$^1_2$, —SO$_2$NR$^1_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —N$^+$R$^1_2$—, —C(O)NR$^1$—, —SO$_2$NR$^1$—, or —P(O)R$^1$—, where R$^1$=non-, partially or perfluorinated $C_1$- to $C_6$-alkyl, $C_3$- to $C_7$-cycloalkyl, unsubstituted or substituted phenyl.

Without restricting generality, examples of substituents R, $R^2$ to $R^{13}$ and $R^{1'}$ to $R^{4'}$ modified in this way are:
—OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SO$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_2$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$FH$_6$, —CH$_2$C$_3$F$_7$, —C(CFH$_2$)$_3$, —CH$_2$C$_6$H$_5$ or P(O)(C$_2$H$_5$)$_2$.

In R$^1$ or R$^{1*}$, $C_3$- to $C_7$-cycloalkyl is, for example, cyclopropyl, cyclobutyl, cyclopentyl, cyclohexyl or cycloheptyl.

In R$^1$ or R$^{1*}$, substituted phenyl denotes phenyl which is substituted by $C_1$- to $C_6$-alkyl, $C_1$- to $C_6$-alkenyl, CN, NR$^1_2$, F, Cl, Br, I, $C_1$-$C_6$-alkoxy, SCF$_3$, SO$_2$CF$_3$ or SO$_2$NR*$_2$, where R* denotes a non-, partially or perfluorinated $C_1$- to $C_6$-alkyl or $C_3$- to $C_7$-cycloalkyl, as defined for R$^1$, for example, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-methoxy-phenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethyl-phenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichloro-phenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxy-phenyl or 2,4,5-trimethylphenyl.

In R$^{1'}$ to R$^{4'}$, heteroaryl is taken to mean a saturated or unsaturated mono- or bicyclic heterocyclic radical having 5 to 13 ring members, where 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, CN, NR$^1_2$, F, Cl, Br, I, $C_1$-$C_6$-alkoxy, SCF$_3$, SO$_2$CF$_3$ or SO$_2$NR$^1_2$, where R$^1$ has an above-mentioned meaning.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is now taken to mean, analogously to aryl-$C_1$-$C_6$-alkyl, for example, pyridinylmethyl, pyridinylethyl, pyridinylpropyl, pyridinyl-butyl, pyridinylpentyl, pyridinylhexyl, where furthermore the heterocycles described above may be linked to the alkylene chain in this way.

HetN+ is preferably

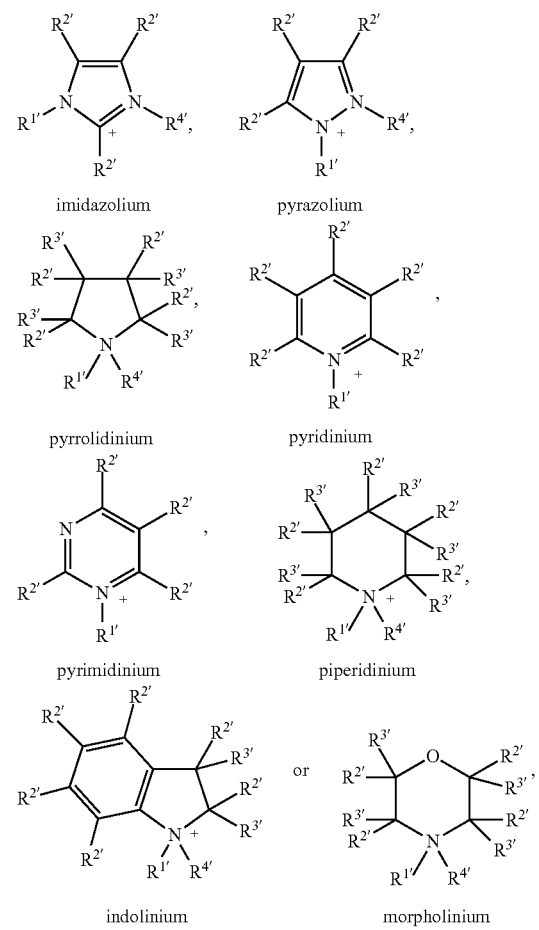

imidazolium pyrazolium pyrrolidinium pyridinium pyrimidinium piperidinium indolinium morpholinium where the substituents R$^{1'}$ to R$^{4'}$ each, independently of one another, have a meaning described above.

The organic cation [Kt]$^{X+}$ is particularly preferably selected from the group comprising imidazolium, pyridinium, pyrrolidinium, ammonium or phosphonium cations, as defined above.

Particularly suitable cations are selected from the group tetraalkylammonium, 1,1-dialkylpyrrolidinium, 1-alkyl-1-alkoxyalkylpyrrolidnium or 1,3-dialkylimidazolium, where the alkyl groups or the alkoxy group in the alkoxyalkyl group may each, independently of one another, have 1 to 10 C atoms. The alkyl groups very particularly preferably have 1 to 6 C atoms and the alkoxy group very particularly preferably has 1 to 3 C atoms. The alkyl groups in tetraalkylammonium may therefore be identical or different. Preferably, three alkyl groups are identical and one alkyl group is different or two alkyl groups are identical and the other two are different. Preferred tetraalkylammonium cations are, for example, trimethyl(ethyl)-ammonium, triethyl(methyl)ammonium, tripropyl(methyl)ammonium, tributyl(methyl)ammonium, tripentyl(methyl)ammonium, trihexyl(methyl)ammonium, triheptyl(methyl)ammonium, trioctyl(methyl)ammonium, trinonyl(methyl)ammonium, tridecyl(methyl)ammonium, trihexyl(ethyl)ammonium, ethyl(trioctyl)ammonium, propyl (dimethyl)ethylammonium, butyl(dimethyl)ethylammonium, methoxyethyl(dimethyl)ethylammonium, methoxyethyl(diethyl)methylammonium, methoxyethyl(dimethyl)propylammonium, ethoxyethyl(dimethyl)ethylammonium. Particularly preferred quaternary ammonium cations are propyl(dimethyl)ethylammonium and/or methoxyethyl(dimethyl)ethylammonium.

Preferred 1,1-dialkylpyrrolidinium cations are, for example, 1,1-dimethylpyrrolidinium, 1-methyl-1-ethylpyrrolidinium, 1-methyl-1-propylpyrrolidinium, 1-methyl-1-butylpyrrolidinium, 1-methyl-1-pentylpyrrolidinium, 1-methyl-1-hexylpyrrolidinium, 1-methyl-1-heptylpyrrolidinium, 1-methyl-1-octylpyrrolidinium, 1-methyl-1-nonylpyrrolidinium, 1-methyl-1-decylpyrrolidinium, 1,1-diethylpyrrolidinium, 1-ethyl-1-propylpyrrolidinium, 1-ethyl-1-butylpyrrolidinium, 1-ethyl-1-pentylpyrrolidinium, 1-ethyl-1-hexylpyrrolidinium, 1-ethyl-1-heptylpyrrolidinium, 1-ethyl-1-octylpyrrolidinium, 1-ethyl-1-nonylpyrrolidinium, 1-ethyl-1-decylpyrrolidinium, 1,1-dipropylpyrrolidinium, 1-propyl-1-methylpyrrolidinium, 1-propyl-1-butylpyrrolidinium, 1-propyl-1-pentylpyrrolidinium, 1-propyl-1-hexylpyrrolidinium, 1-propyl-1-heptylpyrrolidinium, 1-propyl-1-octylpyrrolidinium, 1-propyl-1-nonylpyrrolidinium, 1-propyl-1-decylpyrrolidinium, 1,1-dibutylpyrrolidinium, 1-butyl-1-methylpyrrolidinium, 1-butyl-1-pentylpyrrolidinium, 1-butyl-1-hexylpyrrolidinium, 1-butyl-1-heptylpyrrolidinium, 1-butyl-1-octylpyrrolidinium, 1-butyl-1-nonylpyrrolidinium, 1-butyl-1-decylpyrrolidinium, 1,1-dipentylpyrrolidinium, 1-pentyl-1-hexylpyrrolidinium, 1-pentyl-1-heptylpyrrolidinium, 1-pentyl-1-octylpyrrolidinium, 1-pentyl-1-nonylpyrrolidinium, 1-pentyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-diheptylpyrrolidinium, 1-hexyl-1-heptylpyrrolidinium, 1-hexyl-1-octylpyrrolidinium, 1-hexyl-1-nonylpyrrolidinium, 1-hexyl-1-decylpyrrolidinium, 1,1-dihexylpyrrolidinium, 1-hexyl-1-heptylpyrrolidinium, 1-hexyl-1-octylpyrrolidinium, 1-hexyl-1-nonylpyrrolidinium, 1-heptyl-1-octylpyrrolidinium, 1-heptyl-1-nonylpyrrolidinium, 1-heptyl-1-decylpyrrolidinium, 1,1-dioctylpyrrolidinium, 1-octyl-1-nonylpyrrolidinium, 1-octyl-1-decylpyrrolidinium, 1-1-dinonylpyrrolidinium, 1-nony-1-decylpyrrolidinium or 1,1-didecylpyrrolidinium. Very particular preference is given to 1-butyl-1-methylpyrrolidinium or 1-propyl-1-methylpyrrolidinium.

Preferred 1-alkyl-1-alkoxyalkylpyrrolidinium cations are, for example, 1-(2-methoxyethyl)-1-methylpyrrolidinium, 1-(2-methoxyethyl)-1-ethylpyrrolidinium, 1-(2-methoxyethyl)-1-propylpyrrolidinium, 1-(2-methoxyethyl)-1-butylpyrrolidinium, 1-(2-ethoxyethyl)-1-methylpyrrolidinium, 1-ethoxymethyl-1-methylpyrrolidinium. Very particular preference is given to 1-(2-methoxyethyl)-1-methylpyrrolidinium.

Preferred 1,3-dialkylimidazolium cations are, for example, 1-ethyl-3-methylimidazolium, 1-methyl-3-propylimidazolium, 1-butyl-3-methylimidazolium, 1-methyl-3-pentylimidazolium, 1-ethyl-3-propylimidazolium, 1-butyl-3-ethylimidazolium, 1-ethyl-3-pentylimidazolium, 1-butyl-3-propylimidazolium, 1,3-dimethylimidazolium, 1,3-diethylimidazolium, 1,3-dipropypylimidazolium, 1,3-dibutylimidazolium, 1,3-dipentylimidazolium, 1,3-dihexylimidazolium, 1,3-diheptylimidazolium, 1,3-dioctylimidazolium, 1,3-dinonylimidazolium, 1,3-didecylimidazolium, 1-hexyl-3-methylimidazolium, 1-heptyl-3-methylimidazolium, 1-methyl-3-octylimidazolium, 1-methyl-3-nonylimidazolium, 1-decyl-3-methylimidazolium, 1-ethyl-3-hexylimidazolium, 1-ethyl-3-heptylimidazolium, 1-ethyl-3-octylimidazolium, 1-ethyl-3-nonylimidazolium or 1-decyl-3-ethylimidazolium. Particularly preferred cations are 1-ethyl-3-methylimidazolium, 1-butyl-3-methylimidazolium or 1-methyl-3-propylimidazolium.

Particularly preferred 1-alkenyl-3-alkylimidazolium cations are 1-allyl-3-methylimidazolium or 1-allyl-2,3-dimethylimidazolium.

The organic cations of the compounds of the formula I are preferably heterocyclic cations of the formula (8), where $HetN^{z+}$ is imidazolium, pyrrolidinium or pyridinium, with substituents $R^{1'}$ to $R^{4'}$, each of which has, independently of one another, a meaning indicated or indicated as preferred. The organic cation of the compounds of the formula I are particularly preferably imidazolium, where the substituents $R^{1'}$ to $R^{4'}$ have a meaning mentioned above or a meaning indicated as preferred or they have the meaning of the meanings preferably indicated for 1,1-dialkylpyrrolidinium, 1-alkyl-1-alkoxyalkylalkylpyrrolidinium, 1,3-dialkylimidazolium, 1-alkenyl-3-alkylimidazolium or 1-alkoxyalkyl-3-alkylimidazolium, as described above.

Particularly preferred organic cations of the formula I are accordingly 1-butyl-1-methylpyrrolidinium, 1-ethyl-3-methylimidazolium, 1-ethyl-2,3-dimethylimidazolium, 1-(2-methoxyethyl)-3-methylimidazolium, 1-butyl-3-methylimidazolium, tributylmethylammonium, tetra-n-butylammonium, tributylmethylphosphonium, tetraphenylphosphonium, diethylmethylsulfonium, S-ethyl-N,N,N',N'-tetramethylisothiouronium, 1-allyl-3-methylimidazolium, 1-allyl-2,3-dimethylimidazolium, 1-cyanomethyl-3-methylimidazolium, 1-methyl-3-propynylimidazlium, 1,1-dimethylpyrrolidinium or tri-methylsulfonium.

In an embodiment, the compounds of the formula I are synthesised from the compounds of the formula III by the subsequent salt-exchange reaction with compounds of the formula IV, as described above.

The anion of the formula (IV) is preferably $OH^-$, $Cl^-$, $Br^-$, $I^-$, $[CH_3SO_3]^-$ $[CH_3OSO_3]^-$, $[CF_3COO]^-$, $[CF_3SO_3]^-$, $[(C_2F_5)_2P(O)O]^-$ or $[CO_3]^{2-}$, particularly preferably $OH^-$, $Cl^-$, $Br^-$, $[CH_3OSO_3]^-$, $[CF_3SO_3]^-$, $[CH_3SO_3]$ or $[(C_2F_5)_2P(O)O]^-$.

The reaction is advantageously carried out in water, where temperatures of 0°-100° C., preferably 15°-60° C., are suitable. The reaction is particularly preferably carried out at room temperature (25° C.).

However, the reaction may alternatively also be carried out in organic solvents at temperatures between −30° and 100° C. Suitable solvents here are acetonitrile, dioxane, dichloromethane, dimethoxyethane, dimethyl sulfoxide, tetrahydrofuran, dimethylformamide or alcohol, for example methanol, ethanol or isopropanol.

In an alternative embodiment, depending on the respectively desired organic cation of the compounds of the formula I, a compound of the formula II having an organic cation, as desired for the compound of the formula I, can also be reacted with trialkylsilyl cyanide, as described above. This synthesis is particularly suitable for ammonium or phosphonium cations.

The subject-matter of the main claim, i.e. the process for the preparation of compounds of the formula I, as described above, is thus essentially novel and inventive since the compounds of the formula III can be prepared economically for the first time.

The invention therefore likewise relates to a process for the preparation of compounds of the formula III $$Me^+[B(R_f)(CN)_x(F)_y]^- \quad\quad III,$$

where $Me^+$ is a lithium, potassium, sodium, caesium or rubidium salt, $R_f$ denotes a linear or branched perfluorinated alkyl group having 1 to 4 C atoms, $C_6F_5$, $C_6H_5$, partially fluorinated phenyl, or phenyl which is mono- or disubstituted by a perfluoroalkyl group having 1 to 4 C atoms, where the perfluoroalkyl group is selected independently of one another, a is 1 or 2,
x is 1, 2 or 3,
y is 0, 1 or 2 and
x+y=3, by reaction of an alkali metal salt of the formula II $$Me^+[B(R_f)F_3]^- \quad\quad II,$$

where $Me^+$ and $R_f$ have an above-mentioned meaning, with a trialkylsilyl cyanide, where the alkyl group of the trialkylsilyl cyanide is in each case, independently of one another, a linear or branched alkyl group having 1 to 4 C atoms.

As also described above, this process according to the invention is also characterised in that the reaction for the preparation of compounds of the formula III where x=1, y=2 is carried out at temperatures between 10° C. and 110° C. or with microwave irradiation with 100 W or in that the reaction for the preparation of compounds of the formula III where x=2 and y=1 is carried out at temperatures between 115° C. and 200° C. or with microwave irradiation with 200 W or in that the reaction for the preparation of compounds of the formula III where x=3 and y=0 is carried out with microwave irradiation with greater than 200 W, preferably at 300 W. The same detailed descriptions also apply to this process, which includes a part-step from the process according to the invention in accordance with the main claim.

The invention furthermore also relates to the salts of the formula III, $$Me^+[B(R_f)(CN)_x(F)_y]^- \quad\quad III,$$

where $Me^+$ is a lithium, potassium, sodium, caesium or rubidium salt, $R_f$ denotes a linear or branched perfluorinated alkyl group having 1 to 4 C atoms, $C_6F_5$, $C_6H_5$, partially fluorinated phenyl, or phenyl which is mono- or disubstituted by a perfluoroalkyl group having 1 to 4 C atoms, where the perfluoroalkyl group is selected independently of one another, a is 1 or 2,
x is 1, 2 or 3,
y is 0, 1 or 2, where 0 is excluded for $R_f=C_6H_5$, and
x+y=3.

The invention furthermore also relates to the salts of the formula III, $$Me^+[B(R_f)(ON)_x(F)_y]^- \quad\quad III,$$

where $Me^+$ is a lithium, potassium, sodium, caesium or rubidium salt, $R_f$ denotes a linear or branched perfluorinated alkyl group having 1 to 4 C atoms, $C_6F_5$, $C_6H_5$, partially fluorinated phenyl, or phenyl which is mono- or disubstituted by a perfluoroalkyl group having 1 to 4 C atoms, where the perfluoroalkyl group is selected independently of one another, a is 1 or 2,
x is 1, 2 or 3,
y is 0, 1 or 2, where 0 is excluded for $R_f=C_6H_5$, and
x+y=3, where lithium trifluoromethyldifluoromonocyanoborate, lithium trifluoromethylfluorodicyanoborate, potassium trifluoromethyldifluoromonocyanoborate and potassium trifluoromethylfluorodicyanoborate are excluded.

The potassium and sodium salts are particularly suitable in accordance with the invention for the preparation of the compounds of the formula I, as described above.

The lithium salts of the compounds of the formula III are particularly suitable for the preparation of electrolyte preparations, in particular for electrochemical or opto-electronic devices. The lithium salts of the formula III are particularly suitable as conductive salt for electrochemical batteries, in particular lithium ion batteries, lithium ion capacitors or lithium batteries. They are distinguished over known lithium salts having borate anions, such as, for example, lithium tetrafluoroborate or lithium tetracyanoborate, through the ability of the lithium salts of the formula III to dissolve in high concentration in carbonate-containing solvents. Thus, for example, it has been established that the lithium salt from Example 37 dissolves in diethyl carbonate to give a 2 molar solution and has high electrochemical stability. The use of the lithium salts of the formula III in lithium ion batteries, lithium ion capacitors or lithium batteries would therefore be very particularly advantageous.

The invention therefore furthermore particularly preferably relates to a lithium salt of the formula III.

The following salts are preferred here, where the lithium salts are particularly preferred:
potassium trifluoromethyltricyanoborate, potassium pentafluoroethyltricyanoborate, potassium heptafluoropropyltricyanoborate, potassium trifluoromethyldicyanofluoroborate, potassium pentafluoroethyldicyanofluoroborate, potassium heptafluoropropyldicyanofluoroborate, potassium trifluoromethylmonocyanodifluoroborate, potassium pentafluoromethylmonocyanodifluoroborate, potassium heptafluoropropylmonocyanodifluoroborate, potassium nonafluorobutylmonocyanodifluoroborate, potassium pentafluorophenyltricyanoborate, potassium pentafluorophenyldicyanofluoroborate, potassium pentafluorophenylmonocyanodifluoroborate, potassium phenyldicyanofluoroborate, potassium phenylmonocyanodifluoroborate, potassium p-fluorophenyltricyanoborate, potassium p-fluorophenyldicyanofluoroborate, potassium p-fluorophenylmonocyanodifluoroborate, potassium 3,5-bis(trifluoromethyl)phenyltricyanoborate, potassium 3,5-bis(trifluoromethyl)phenyldicyanofluoroborate or potassium 3,5-bis(trifluoromethyl)phenylmonocyanodifluoroborate, lithium trifluoromethyltricyanoborate, lithium pentafluoroethyltricyanoborate, lithium heptafluoropropyltricyanoborate, lithium trifluoromethyldicyanofluoroborate, lithium pentafluoroethyldicyanofluoroborate, lithium heptafluoropropyldicyanofluoroborate, lithium trifluoromethylmonocyanodifluoroborate, lithium pentafluoromethylmonocyanodifluoroborate, lithium heptafluoropropylmonocyanodifluoroborate, lithium nonafluorobutylmonocyanodifluoroborate, lithium pentafluorophenyltricyanoborate, lithium pentafluorophenyldicyanofluoroborate, lithium pentafluorophenylmonocyanodifluoroborate, lithium phenyldicyanofluoroborate, lithium phenylmonocyanodifluoroborate, lithium p-fluorophenyltricyanoborate, lithium p-fluorophenyldicyanofluoroborate, lithium p-fluorophenylmonocyanodifluoroborate, lithium 3,5-bis(trifluoromethyl)phenyltricyanoborate, lithium 3,5-bis(trifluoromethyl)phenyldicyanofluoroborate or lithium 3,5-bis(trifluoromethyl)phenylmonocyanodifluoroborate, sodium trifluoromethyltricyanoborate, sodium pentafluoroethyltricyanoborate, sodium heptafluoropropyltricyanoborate, sodium trifluoromethyldicyanofluoroborate, sodium pentafluoroethyldicyanofluoroborate, sodium heptafluoropropyldicyanofluoroborate, sodium trifluoromethylmonocyanodifluoroborate, sodium pentafluoromethylmonocyanodifluoroborate, sodium heptafluoropropylmonocyanodifluoroborate, sodium nonafluorobutylmonocyanodifluoroborate, sodium pentafluorophenyltricyanoborate, sodium pentafluorophenyldicyanofluoroborate, sodium pentafluorophenylmonocyanodifluoroborate, sodium phenyldicyanofluoroborate, sodium phenylmonocyanodifluoroborate, sodium p-fluorophenyltricyanoborate, sodium p-fluorophenyldicyanofluoroborate, sodium p-fluorophenylmonocyanodifluoroborate, sodium 3,5-bis(trifluoromethyl)phenyltricyanoborate, sodium 3,5-bis(trifluoromethyl)phenyldicyanofluoroborate or sodium 3,5-bis(trifluoromethyl)phenylmonocyanodifluoroborate, caesium trifluoromethyltricyanoborate, caesium pentafluoroethyltricyanoborate, caesium heptafluoropropyltricyanoborate, caesium trifluoromethyldicyanofluoroborate, caesium pentafluoroethyldicyanofluoroborate, caesium heptafluoropropyldicyanofluoroborate, caesium trifluoromethylmonocyanodifluoroborate, caesium pentafluoromethylmonocyanodifluoroborate, caesium heptafluoropropylmonocyanodifluoroborate, caesium nonafluorobutylmonocyanodifluoroborate, caesium pentafluorophenyltricyanoborate, caesium pentafluorophenyldicyanofluoroborate, caesium pentafluorophenylmonocyanodifluoroborate, caesium phenyldicyanofluoroborate, caesium phenylmonocyanodifluoroborate, caesium p-fluorophenyltricyanoborate, caesium p-fluorophenyldicyanofluoroborate, caesium p-fluorophenylmonocyanodifluoroborate, caesium 3,5-bis(trifluoromethyl)phenyltricyanoborate, caesium 3,5-bis(trifluoromethyl)phenyldicyanofluoroborate or caesium 3,5-bis(trifluoromethyl)phenylmonocyanodifluoroborate, rubidium trifluoromethyltricyanoborate, rubidium pentafluoroethyltricyanoborate, rubidium heptafluoropropyltricyanoborate, rubidium trifluoromethyldicyanofluoroborate, rubidium pentafluoroethyldicyanofluoroborate, rubidium heptafluoropropyldicyanofluoroborate, rubidium trifluoromethylmonocyanodifluoroborate, rubidium pentafluoromethylmonocyanodifluoroborate, rubidium heptafluoropropylmonocyanodifluoroborate, rubidium nonafluorobutylmonocyanodifluoroborate, rubidium pentafluorophenyltricyanoborate, rubidium pentafluorophenyldicyanofluoroborate, rubidium pentafluorophenylmonocyanodifluoroborate, rubidium phenyldicyanofluoroborate, rubidium phenylmonocyanodifluoroborate, rubidium p-fluorophenyltricyanoborate, rubidium p-fluorophenyldicyanofluoroborate, rubidium p-fluorophenylmonocyanodifluoroborate, rubidium 3,5-bis(trifluoromethyl)phenyltricyanoborate, rubidium 3,5-bis(trifluoromethyl)phenyldicyanofluoroborate or rubidium 3,5-bis(trifluoromethyl)phenylmonocyanodifluoroborate.

The invention accordingly furthermore also relates to an electrolyte comprising a compound of the formula III, $$Me^+[B(R_f)(CN)_x(F)_y]^- \quad \text{III,}$$

where $Me^+$ is a lithium, potassium, sodium, caesium or rubidium salt, $R_f$ denotes a linear or branched perfluorinated alkyl group having 1 to 4 C atoms, $C_6F_5$, $C_6H_5$, partially fluorinated phenyl or phenyl which is mono- or disubstituted by a perfluoroalkyl group having 1 to 4 C atoms, where the perfluoroalkyl group is selected independently of one another, a is 1 or 2,
x is 1, 2 or 3,
y is 0, 1 or 2, and
x+y=3, or described as preferred.

The invention accordingly furthermore also relates to an electrochemical cell containing a compound of the formula III, as described above as constituent for the electrolyte or described as preferred or to an electrolyte comprising these compounds.

In particular, a lithium ion battery, a lithium ion capacitor or a lithium battery are particularly preferred as electrochemical cell.

The following working examples are intended to explain the invention without limiting it. The invention can be carried out correspondingly throughout the range claimed. Possible variants can also be derived starting from the examples. In particular, the features and conditions of the reactions described in the examples can also be applied to other reactions which are not shown in detail, but fall within the scope of protection of the claims.

EXAMPLES

The substances obtained are characterised by means of Raman spectroscopy, elemental analysis and NMR spectroscopy. The NMR spectra are measured on solutions in deuterated acetone-$D_6$ in a Bruker Avance III spectrometer with deuterium lock. The measurement frequencies of the various nuclei are: $^1H$, 400.17 MHz, $^{19}F$: 376.54 MHz, $^{11}B$: 128.39 MHz, $^{31}P$: 161.99 MHz and $^{13}C$: 100.61 MHz. The referencing is carried out with an external reference: TMS for $^1H$ and $^{13}C$ spectra; $CCl_3F$— for $^{19}F$ and $BF_3.Et_2O$— for $^{11}B$ spectra.

For the anions in the compounds described below, the following values are measured in $^{13}C$-NMR spectra (solvent: acetone-$D_6$ and reference substance: TMS):

$[C_2F_5BF_2(CN)]^-$
$^{13}C$-NMR: δ, ppm=129.66 q, t (CN, 1C); 120.80 q, t ($CF_3$, 1C); 116.90 m ($CF_2$, 10).

$[C_2F_5BF(CN)_2]^-$
$^{13}C$-NMR: δ, ppm=128.18 q, t (2CN, 2C); 121.88 q, t ($CF_3$, 1C); 117.60 m ($CF_2$, 1C).

$[C_2F_5B(CN)_3]^-$
$^{13}C$-NMR: δ, ppm=123.46 q (3CN, 3C); 121.10 q, t ($CF_3$, 1C); 118.20 m ($CF_2$, 1C).

$[CF_3B(CN)_3]^-$
$^{13}C$-NMR: δ, ppm=123.62 q (3CN, 3C); 130.33 q, q ($CF_3$, 1C).

Example 1

Potassium trifluoropentafluoroethylborate—K[$C_2F_5BF_3$]

Pentafluoroethyl iodide $C_2F_5I$ (1.5 g, 6.1 mmol) is condensed into a 100 ml reaction vessel with a glass valve and a PTFE spindle (Young, London) and a magnetic stirrer bar and subsequently dissolved in 50 ml of diethyl ether and reacted at −78° C. with a solution of ethylmagnesium bromide in diethyl ether (2.0 ml, 6.1 mmol, 3 mol l$^{-1}$) and stirred at −78° C. for 1 hour. The reaction mixture is subsequently added at −78° C. to trimethoxyborane (1.2 ml, 10.8 mmol). The mixture is slowly warmed to room temperature. Spray-dried KF (1.3 g, 22.4 mmol) is added to the suspension, and this is stirred at room temperature for a further hour. The reaction mixture is subsequently washed with 50 ml of THF in a PFA flask, and all volatile constituents are distilled off. 10 ml of anhydrous HF are added to the solid, and the mixture is stirred at room temperature for several hours. The HF is removed in vacuo, and the solid is taken up in 15 ml of acetonitrile and filtered. The resultant solution of K[$C_2F_5BF_3$] in acetonitrile (about 0.29 mol l$^{-1}$) can be used directly for the preparation of compounds of the formula III or, after removal of the solvent, converted into K[$C_2F_5BF_2(CN)$], K[$C_2F_5BF(CN)_2$] or K[$C_2F_5B(CN)_3$] in accordance with Example 5, 6 or 7.

Example 2

Potassium cyanodifluorotrifluoromethylborate—K[$CF_3BF_2(CN)$]

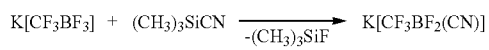

Potassium trifluorotrifluoromethylborate, K[$CF_3BF_3$] (3.0 g, 17.0 mmol), is weighed out into a cylindrical reaction vessel with a glass valve and a PTFE spindle (Young, London) and a magnetic stirrer bar. Trimethylsilyl cyanide (6.0 ml, 45.0 mmol) is added in an argon atmosphere. The reaction mixture is stirred at room temperature for 20 hours. All volatile constituents are removed in vacuo, and most of the unreacted trimethylsilyl cyanide (3.0 ml, 22.5 mmol) is recovered by fractional distillation. The solid residue is taken up in THF (3 ml), and K[$CF_3BF_2CN$] is precipitated by addition of $CH_2Cl_2$ (150 ml) and subsequently filtered off. The colourless solid is dried in vacuo. Yield, based on the potassium trifluorotrifluoromethylborate employed: 3.0 g (16.4 mmol, 96%). Decomposition from 200° C.

Raman spectroscopy: $\tilde{v}$ (CN)=2226 cm$^{-1}$.

$^{11}$B-NMR: δ, ppm=−3.8 tq (1B), $^1J_{F,B}$=49.0 Hz, $^2J_{F,F}$=34.5 Hz.

$^{19}$F-NMR: δ, ppm=−77.4 q (CF$_3$, 3F), $^2J_{F,B}$=34.5 Hz; −169.1 q (BF$_2$, 2F), $^1J_{F,B}$=49.3 Hz Elemental analysis. Found, %, C, 13.29, N, 7.62; calculated for $C_2BF_5KN$, %, C, 13.13, N, 7.66.

Example 3

Potassium dicyanofluorotrifluoromethylborate—K[$CF_3BF(CN)_2$]

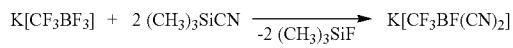

microwave irradiation 200 W, 15 min

Potassium trifluorotrifluoromethylborate, K[$CF_3BF_3$] (6.0 g, 34.1 mmol), is weighed out into a cylindrical reaction vessel with a glass valve and a PTFE spindle (Young, London) and a magnetic stirrer bar. Trimethylsilyl cyanide (17.1 ml, 127.5 mmol) is added under argon. The reaction mixture is stirred at room temperature for 12 days. Most of the trimethylsilyl fluoride formed is removed in vacuo. The reaction mixture is subsequently irradiated in a microwave (CEM Discover) (200 W, T$_{max}$=90° C., 20 minutes). All volatile constituents are removed in vacuo, and most of the unreacted trimethylsilyl cyanide (6.3 ml, 47.2 mmol) is recovered by fractional distillation. The residue is taken up in aqueous $H_2O_2$ (30%, 50 ml) and stirred for one hour. The pH of the solution is adjusted to 1 using 37% hydrochloric acid. N(C$_3$H$_7$)$_3$ (7.0 ml, 36.8 mmol) is added to the reaction mixture, and the tripropylammonium salt is extracted with $CH_2Cl_2$ (3×50 ml). The combined organic phases are dried using MgSO$_4$, filtered, and an aqueous potassium hydroxide solution (6 g, 30 ml) is added. The organic phase is decanted off, a second portion of an aqueous KOH solution (6 g, 30 ml) is added, and the organic phase is decanted off again. The aqueous phases are extracted with THF (3×50 ml). The collected tetrahydrofuran fractions are dried using $K_2CO_3$, filtered and evaporated. K[$CF_3BF(CN)_2$] is precipitated by addition of $CH_2Cl_2$ (150 ml) and is dried in vacuo. Yield, based on the potassium trifluorotrifluoromethylborate employed: 5.0 g (26.3 mmol, 77%). Decomposition from 260° C.;

Raman spectroscopy: $\tilde{v}$ (CN)=2215 cm$^{-1}$.

$^{11}$B-NMR: δ, ppm=−12.8 dq (1B), $^1J_{F,B}$=49.3 Hz, $^2J_{F,B}$=35.7 Hz.

$^{19}$F-NMR: δ, ppm=−74.0 qd (CF$_3$, 3F), $^2J_{F,B}$=35.7 Hz, $^3J_{F,F}$=8.3 Hz;

−219.7 qq (BF, 1F), $^1J_{F,B}$=49.2 Hz, $^3J_{F,F}$=8.0 Hz

Example 4

Potassium tricyanotrifluoromethylborate—K[$CF_3B(CN)_3$]

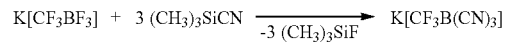

microwave irradiation 300 W, 95 min

Potassium trifluorotrifluoromethylborate, K[$CF_3BF_3$] (0.5 g, 2.8 mmol), are weighed out into a cylindrical reaction vessel with a glass valve and a PTFE spindle (Young, London) and a magnetic stirrer bar. Trimethylsilyl cyanide (10.0 ml, 74.9 mmol) is added in an argon atmosphere. The reaction mixture is stirred at 100° C. for 2 hours. Most of the trimethylsilyl fluoride formed is subsequently removed in vacuo, and the reaction mixture is irradiated in a microwave (CEM Discover) (300 W, T$_{max}$=120° C., 95 minutes). All volatile constituents are subsequently removed under reduced pressure, and most of the unreacted trimethylsilyl cyanide (8.0 ml, 59.9 mmol) is recovered by fractional distillation. The residue is dissolved in 30% aqueous $H_2O_2$ (5 ml). $K_2CO_3$ is added to the solution, which is then stirred for one h. The mixture is evaporated to dryness using a rotary evaporator, and the residue is extracted with diethyl ether (3×50 ml). The volume of the combined ethereal phases is reduced to 5 ml, and the addition of $CH_2Cl_2$ (100 ml) gives colourless K[$CF_3B(CN)_3$]. The potassium salt is filtered off and dried in vacuo. Yield, based on the potassium trifluorotrifluoromethylborate employed: 0.53 g (2.74 mmol, 95%).

Decomposition from 320° C.; Raman spectroscopy: $\tilde{v}$ (CN)=2237, 2231 cm$^{-1}$.

$^{11}$B-NMR: δ, ppm=−32.0 q (1B), $^2J_{F,B}$=36.3 Hz.

$^{19}$F-NMR: δ, ppm=−66.4 q (CF$_3$, 3F), $^2J_{F,B}$=36.3 Hz

Example 5

Potassium cyanodifluoropentafluoroethylborate—K[C₂F₅BF₂(CN)]

A.

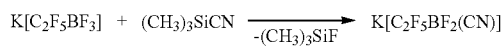

Potassium trifluoropentafluoroethylborate, K[C₂F₅BF₃] (10.4 g, 46.0 mmol), is weighed out into a cylindrical reaction vessel with a glass valve and a PTFE spindle (Young, London) and a magnetic stirrer bar. The flask is secured, and trimethylsilyl cyanide (70.0 ml, 524.9 mmol) is added in an argon atmosphere. The reaction mixture is stirred at 100° C. for 45 min, and the trimethylsilyl fluoride formed in the process is distilled off continuously. All volatile constituents are subsequently removed in vacuo. Most of the unreacted trimethylsilyl cyanide (58.1 ml, 159.9. mmol) is recovered by fractional distillation. The residue is washed with CH₂Cl₂ (200 ml), filtered and dried in vacuo. Potassium cyanodifluoropentafluoroethylborate, K[C₂F₅BF₂(CN)], is obtained as colourless solid. Yield, based on the potassium trifluoropentafluoroethylborate employed: 9.8 g (42.1 mmol, 92%). Decomposition from 260° C.; Raman spectroscopy: ṽ (CN)= 2235 cm⁻¹.

$^{11}$B-NMR: δ, ppm=−2.7 tt (1B), $^{1}J_{F,B}$=51.0 Hz, $^{2}J_{F,B}$=25.3 Hz $^{19}$F-NMR: δ, ppm=−83.3 t (CF₃, 3F), $^{4}J_{F,B}$=5.2 Hz; -136.3 q (CF₂, 2F), $^{2}J_{F,B}$=23.3 Hz; -167.2 qq (BF₂, 2F), $^{1}J_{F,B}$=51.1 Hz, $^{4}J_{F,F}$=5.1 Hz

B.

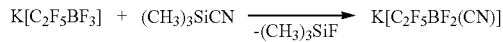

A cylindrical reaction vessel with a glass valve and a PTFE spindle (Young, London) and a magnetic stirrer bar is filled with potassium trifluoropentafluoroethylborate, K[C₂F₅BF₃] (15.8 g, 69.9 mmol). Trimethylsilyl cyanide (35.0 ml, 262.5 mmol) is added in a protective-gas atmosphere. The reaction mixture is stirred at 100° C. for 1 hour, and the trimethylsilyl fluoride formed is distilled off continuously. All volatile constituents are subsequently removed in vacuo. Most of the unreacted trimethylsilyl cyanide (21.3 ml, 159.9 mmol) is recovered by fractional distillation. The residue is dissolved in THF (5 ml), and colourless potassium cyanodifluoropentafluoroethylborate, K[C₂F₅BF₂(CN)], is precipitated by addition of CH₂Cl₂ (200 ml), subsequently filtered off and dried in vacuo. Yield, based on the potassium trifluoropentafluoroethylborate employed: 15.8 g (67.8 mmol, 97%). $^{11}$B and $^{19}$F NMR spectra correspond to the values indicated in Example 5,A.

Elemental analysis. Found, %, C, 15.24, N, 5.78; calculated for C₃BF₇KN, %, C, 15.47, N, 6.01.

C.

In a dry box, K[C₂F₅BF₃] (100 mg, 0.44 mmol), LiCl (180 mg, 4.2 mmol) and KCN (260 mg, 3.99 mmol) are finely ground together and introduced into a cylindrical reaction vessel with a glass valve and a PTFE spindle (Young, London). The reaction mixture is heated at 180° C. for 20 hours in vacuo. The $^{11}$B-NMR spectroscopic analysis shows that the reaction mixture comprises the following borate anions:

| Anion | δ($^{11}$B) [ppm] | Proportion in % |
|---|---|---|
| [C₂F₅BF₂(CN)]⁻ | −2.8 | 82 |
| [BF₂(CN)₂]⁻ | −7.3 | 5 |
| [BF(CN)₃]⁻ | −17.8 | 4 |
| unknown | −20.5 | 1 |
| [B(CN)₄]⁻ | −38.5 | 6 |

Example 6

Potassium dicyanofluoropentafluoroethylborate—K[C₂F₅BF(CN)₂]

A.

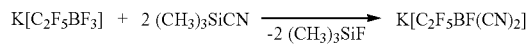

Potassium trifluoropentafluoroethylborate, K[C₂F₅BF₃] (1.0 g, 4.4 mmol), is dissolved in trimethylsilyl cyanide (10.0 ml, 74.9 mmol) in an argon atmosphere in a cylindrical reaction vessel with a glass valve and a PTFE spindle (Young, London) and a magnetic stirrer bar. The reaction mixture is stirred at 110° C. for 1 hour, and the trimethylsilyl fluoride forming is distilled off continuously. The reaction mixture is subsequently stirred at 180° C. in 10 intervals of about 30 minutes each, cooled, and most of the trimethylsilyl fluoride formed is removed. All volatile constituents are subsequently removed in vacuo. Most of the unreacted trimethylsilyl cyanide (7.1 ml, 53.0 mmol) is purified by fractional distillation. The residue is dissolved in THF (3 ml), and colourless K[C₂F₅BF(CN)₂] is precipitated by addition of CH₂Cl₂ (100 ml). The salt is filtered off and dried in vacuo. Yield, based on the potassium trifluoropentafluoroethylborate employed: 0.97 g (4.0 mmol, 92%).

Decomposition from 260° C.; Raman spectroscopy: ṽ (CN)=2224 cm⁻¹.

$^{11}$B-NMR: δ, ppm=−12.0 dt (1B), $^{1}J_{F,F}$=51.6 Hz, $^{2}J_{F,F}$=25.2 Hz.

$^{19}$F-NMR: δ, ppm=−82.6 dt (CF₃, 3F), $^{3}J_{F,F}$=1.0 Hz, $^{4}J_{F,F}$=6.3 Hz; −132.0 qd (CF₂, 2F), $^{3}J_{F,F}$=5.0 Hz, $^{2}J_{F,B}$=25.3 Hz; −219.1 qqt (BF, 1F), $^{1}J_{F,B}$=52 Hz, $^{3}J_{F,F}$=5-6 Hz, $^{4}J_{F,F}$=5-6 Hz.

Trimethylsilyl cyanide (10.0 ml, 74.9 mmol) is added to potassium trifluoropentafluoroethylborate, K[C₂F₅BF₃] (1.0 g, 4.4 mmol), in an argon atmosphere in a cylindrical reaction vessel with a glass valve and a PTFE spindle (Young, London) and a magnetic stirrer bar. The reaction mixture is stirred at 150° C. for 52 hours with regular degassing. All volatile constituents are subsequently removed in vacuo. Most of the unreacted trimethylsilyl cyanide (7.1 ml, 53.0 mmol) is recovered by fractional distillation. Colourless K[C₂F₅BF(CN)₂] is precipitated from THF (3 ml) using CH₂Cl₂ (100 ml), filtered and dried in vacuo. Yield, based on the potassium trifluoropentafluoroethylborate employed: 0.95 g (3.9 mmol, 90%).

C.

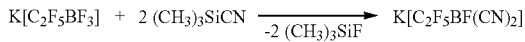

microwave irradiation 200 W, 15 min

Potassium trifluoropentafluoroethylborate, K[C$_2$F$_5$BF$_3$] (5.0 g, 22.1 mmol), is weighed out into a cylindrical reaction vessel with a glass valve and a PTFE spindle (Young, London) and a magnetic stirrer bar. The flask is evacuated, and trimethylsilyl cyanide (10.0 ml, 74.9 mmol) is condensed in. The reaction mixture is irradiated in a microwave (CEM Discover) (200 W, T$_{max}$=70° C.) for 15 min. All volatile constituents are removed in vacuo, and most of the unreacted trimethylsilyl cyanide (3.1 ml, 23.1 mmol) is recovered by fractional distillation. The residue is dissolved in 30% aqueous H$_2$O$_2$ (200 ml), and the solution is adjusted to pH=1 by addition of 37% hydrochloric acid with stirring. N(C$_3$H$_7$)$_3$ (7.0 ml, 36.8 mmol) is subsequently added. The mixture is extracted with CH$_2$Cl$_2$ (2×100 and 1×50 ml). The combined organic phases are dried using MgSO$_4$, filtered, and an aqueous KOH solution (6 g, 30 ml) is added. The organic phase is decanted off, and a second portion of an aqueous KOH solution (10 g, 40 ml) is added, and the mixture is stirred for one hour. The organic phase is then separated off, and the aqueous phase is extracted with Et$_2$O (3×100 ml). In each of the three extraction steps, more K$_2$CO$_3$ is added to the aqueous phase. The collected ethereal phases are dried using K$_2$CO$_3$, filtered and evaporated to dryness. The residue obtained is suspended in CH$_2$Cl$_2$ (50 ml), filtered and dried in vacuo. Yield of potassium dicyanofluoropentafluoroethylborate, K[C$_2$F$_5$BF(CN)$_2$], is 3.4 g (14.3 mmol, 65%), based on the potassium trifluoropentafluoroethylborate employed. $^{11}$B and $^{19}$F NMR spectra correspond to the values indicated in Example 6,A.

D.

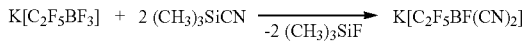

microwave irradiation 200 W, 15 min

Trimethylsilyl cyanide (25.0 ml, 187.5 mmol) is added in an argon atmosphere to potassium trifluoropentafluoroethylborate, K[C$_2$F$_5$BF$_3$] (8.0 g, 35.4 mmol), in a cylindrical reaction vessel with a glass valve and a PTFE spindle (Young, London) and a magnetic stirrer bar. The reaction mixture is stirred at room temperature for 3 days. The mixture is degassed and subsequently irradiated in a microwave (CEM Discover) (200 W, T$_{max}$=78° C.) for 15 minutes. All volatile constituents are removed in vacuo, and most of the unreacted trimethylsilyl cyanide (13.5 ml, 101.5 mmol) is recovered by fractional distillation. The residue is dissolved in 30% H$_2$O$_2$ (20 ml), and K$_2$CO$_3$ (5 g) is added. The mixture is stirred at room temperature for 1 hour. The solution is evaporated to dryness at 70° C. in a rotary evaporator, and the solid obtained is extracted with Et$_2$O (7×50 ml). The combined organic phases are dried over K$_2$CO$_3$, filtered and evaporated to dryness. The residue is dissolved in acetone (5 ml). Colourless potassium dicyanofluoropentafluoroethylborate, K[C$_2$F$_5$BF(CN)$_2$], is obtained by addition of CH$_2$Cl$_2$ (150 ml), filtered and dried in vacuo. Yield, based on the potassium trifluoropentafluoroethylborate employed: 7.8 g (32.5 mmol, 92%). $^{11}$B and $^{19}$F NMR spectra correspond to the values indicated in Example 6,A.

Example 7

Potassium tricyanopentafluoroethylborate—K[C$_2$F$_5$B(CN)$_3$]

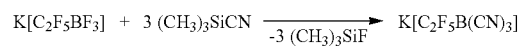

microwave irradiation 300 W, 60 min

Potassium trifluoropentafluoroethylborate, K[C$_2$F$_5$BF$_3$] (0.5 g, 2.2 mmol), is weighed out into a cylindrical reaction vessel with a glass valve and a PTFE spindle (Young, London) and a magnetic stirrer bar. The flask is secured, and trimethylsilyl cyanide (10.0 ml, 74.9 mmol) is added in an argon atmosphere. The reaction mixture is stirred at room temperature for 2 days and subsequently irradiated in a microwave (CEM Discover) (300 W, T$_{max}$=120° C., 60 min). All volatile constituents are removed in vacuo, and most of the unreacted trimethylsilyl cyanide (6.9 ml, 52.0 mmol) is recovered by fractional distillation. The residue is dissolved in 30% aqueous H$_2$O$_2$ (10 ml), and K$_2$CO$_3$ (2 g) is added. The mixture is stirred at room temperature for 1 hour. The solution is evaporated to dryness at 80° C. using a rotary evaporator. The solid remaining is extracted with Et$_2$O (4×50 ml). The combined organic phases are dried using K$_2$CO$_3$, filtered and evaporated to a residual volume of 5 ml. A colourless precipitate is obtained by slow addition of CH$_2$Cl$_2$ (150 ml). The colourless K[C$_2$F$_5$B(CN)$_3$] is filtered off and dried in vacuo. Yield, based on the potassium trifluoropentafluoroethylborate employed: 480 mg (1.9 mmol, 88%).

Decomposition from 350° C.; Raman spectroscopy: ṽ (CN)=2236, 2232 cm$^{-1}$.

$^{11}$B-NMR: δ, ppm=−31.9 t (1B), $^2J_{F,B}$=25.2 Hz.

$^{19}$F-NMR: δ, ppm=−82.3 s (CF$_3$, 3F); -124.2 q (CF$_2$, 2F), $^2J_{F,B}$=25.2 Hz.

Elemental analysis. Found, %, C, 24.10, N, 16.06; calculated for C$_5$BF$_5$KN$_3$, %, C, 24.32, N, 17.01.

Example 8

Potassium cyanodifluoropentafluorophenylborate—K[C$_6$F$_5$BF$_2$(CN)]

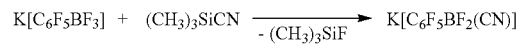

Potassium trifluoropentafluorophenylborate, K[C$_6$F$_5$BF$_3$] (2.5 g, 9.3 mmol), is weighed out into a cylindrical reaction vessel with a glass valve and a PTFE spindle (Young, London) and a magnetic stirrer bar. Trimethylsilyl cyanide (10.0 ml, 74.9 mmol) is added in a protective-gas atmosphere. The reaction mixture is stirred at room temperature for 7 days. All volatile constituents are removed in vacuo, and most of the unreacted trimethylsilyl cyanide (7.7 ml, 57.9 mmol) is recovered by fractional distillation. The residue is dissolved in acetone (5 ml). Colourless K[C$_6$F$_5$BF$_2$CN] is precipitated by addition of CHCl$_3$ (25 ml). Yield, based on the potassium trifluoropentafluorophenylborate employed: 2.1 g (7.5 mmol, 82%).

Decomposition from 190° C.; Raman spectroscopy: v (CN)=2224 cm$^{-1}$.

$^{11}$B-NMR: δ, ppm=−1.3 t, $^{1}J_{F,B}$=52 Hz.

$^{19}$F-NMR: δ, ppm=−136.4 m (2F), −151.1 tq (2F, BF$_2$), $^{1}J_{B,F}$=52 Hz, $^{4}J_{F,F}$=14 Hz; −161.9 t (1F), $^{3}J_{F,F}$=19 Hz; −167.2 m (2F).

Example 9

Potassium tricyanopentafluorophenylborate—K[C$_6$F$_5$B(CN)$_3$]

$$K[C_6F_5BF_3] + 3(CH_3)_3SiCN \xrightarrow{-3(CH_3)_3SiF} K[C_6F_5B(CN)_3]$$

A suspension of potassium trifluoropentafluorophenylborate, K[C$_6$F$_5$BF$_3$] (2.0 g, 7.3 mmol), in trimethylsilyl cyanide (15.0 ml, 112.5 mmol) is introduced into a 50 ml two-necked flask with a stirrer bar and with a reflux condenser in a counterstream of argon. The reaction mixture is heated under reflux for 3 days, and all volatile constituents are distilled off, and most of the unreacted trimethylsilyl cyanide (10.8 ml, 81.1 mmol) is recovered by fractional distillation. The residue is taken up in THF (80 ml) with addition of K$_2$CO$_3$ and filtered. The filtrate is evaporated to a volume of 10 ml, and virtually colourless K[C$_6$F$_5$B(CN)$_3$] is precipitated by slow addition of CHCl$_3$ (100 ml). The precipitate is filtered and dried in vacuo. Yield of potassium tricyanopentafluorophenylborate, K[C$_6$F$_5$B(CN)$_3$], is 1.7 g (5.9 mmol), 81%, based on the potassium trifluoropentafluorophenylborate employed.

Decomposition from 280° C.

$^{11}$B-NMR: δ, ppm=−33.8 t, $^{3}J_{F,B}$=7 Hz.

$^{19}$F-NMR: δ, ppm=−132.0 m (1F), −158.7 t (2F), $^{3}J_{F,F}$=19 Hz; −165.4 m (2F).

Example 10

Tetra-n-butylammonium cyanodifluorotrifluoromethylborate—[(n-C$_4$H$_9$)$_4$NHCF$_3$BF$_2$(CN)]

A.

$$K[CF_3BF_2(CN)] + [(C_4H_9)_4N]Br \xrightarrow{H_2O} [(C_4H_9)_4N][CF_3BF_2(CN)]\downarrow + KBr$$

Potassium cyanodifluorotrifluoromethylborate, K[CF$_3$BF$_2$CN] (0.5 g, 2.7 mmol), prepared as described in Example 2, is dissolved in deionised water (20 ml), and an aqueous solution of [nBu$_4$N]Br (1.7 g, 5.4 mmol, 20 ml) is slowly added with stirring. The colourless precipitate formed is filtered off and dried in vacuo. Yield of tetra-n-butylammonium cyanodifluorotrifluoromethylborate is 0.7 g (1.9 mmol), 67%, based on the potassium cyanodifluorotrifluoromethylborate employed.

Melting point: 73° C.; Raman spectroscopy: ṽ (CN)=2208 cm$^{-1}$.

$^{1}$H-NMR: δ, ppm=1.0 t (4-CH$_3$, 12H), $^{3}J_{H,H}$=7 Hz; 1.4 m (4-CH$_2$, 8H), $^{3}J_{H,H}$=7 Hz, 1.7-1.8 m (4CH$_2$, 8H); 3.3-3.5 m, (4-CH$_2$, 8H).

$^{13}$C{$^{1}$H}-NMR (cation): δ, ppm=59.3 s (4C), 24.3 s (4C), 20.2 s (4C), 13.7 s(4C).

$^{11}$B-NMR: δ, ppm=−3.8 tq (1B), $^{1}J_{F,B}$=49.0 Hz, $^{2}J_{F,B}$=34.5 Hz.

$^{19}$F-NMR: δ, ppm=−77.4 q (CF$_3$, 3F), $^{2}J_{F,B}$=34.5 Hz; −169.1 q (BF$_2$, 2F), $^{1}J_{F,B}$=49.3 Hz Elemental analysis. Found, %, C, 57.19; H, 9.36; N, 7.44; calculated for C$_{18}$H$_{36}$BF$_5$N$_2$, %, C, 55.97; H, 9.39; N, 7.25.

B.

$$K[CF_3BF_3] + (CH_3)_3SiCl + NaCN + [(C_4H_9)_4N]Br \xrightarrow{-(CH_3)_3SiF}$$
$$[(C_4H_9)_4N][CF_3BF_2(CN)] + NaCl + KBr$$

Sodium cyanide (13.1 g, 267.3 mmol) and sodium iodide (3.8 g, 25.4 mmol) are dried at 130° C. in vacuo in 4 hours in a cylindrical reaction vessel with a glass valve and a PTFE spindle (Young, London) and a magnetic stirrer bar. Acetonitrile (15 ml) and trimethylsilyl chloride (30.0 ml, 25.8 g, 237.5 mmol) are subsequently added. The suspension is stirred at 50° C. for 24 hours and at room temperature for 3 days. K[CF$_3$BF$_3$] (0.5 g, 2.8 mmol) is then added in a counterstream of argon, and the reaction mixture is stirred at 50° C. for 24 hours and subsequently at 80° C. for 4 days. All volatile constituents are removed at room temperature in vacuo. Trimethylsilyl cyanide (28.2 ml, 211.2 mmol) is isolated as by-product from the condensed-off phase by fractional distillation and is employed in further reactions. The solid residue obtained is taken up in deionised water (15 ml). 30% aqueous H$_2$O$_2$ (25 ml) and K$_2$CO$_3$ are added to the resultant solution with stirring, and the mixture is stirred for one hour. The solution is evaporated to dryness in vacuo, and the residue is extracted with acetone (3×50 ml). Deionised water 30 ml) is added to the combined organic phases, and the acetone is removed in vacuo. Pure [nBu$_4$N][CF$_3$BF$_2$(CN)] is obtained by addition of a solution of [nBu$_4$N]Br (1.0 g, 3.1 mmol) in deionised water (20 ml). Yield of tetra-n-butylammonium cyanodifluorotrifluoromethylborate is 0.9 g (2.4 mmol), 86%, based on the potassium cyanodifluorotrifluoromethylborate employed.

$^{1}$H and $^{13}$C NMR spectra correspond to the values indicated in Example 10,A.

Example 11

1-Ethyl-3-methylimidazolium cyanodifluorotrifluoromethylborate—[C$_6$H$_{11}$N$_2$][CF$_3$BF$_2$(CN)]

$$C_2H_5-N{\overset{+}{\frown}}N-CH_3 \; Cl^- + K[CF_3BF_2(CN)] \xrightarrow{H_2O}$$
$$C_2H_5-N{\overset{+}{\frown}}N-CH_3 + KCl$$
$$[CF_3BF_2(CN)]^- \downarrow$$

K[CF$_3$BF$_2$(CN)] (5.9 g, 32.5 mmol), prepared as described in Example 2, is added with vigorous stirring to a solution of 1-ethyl-3-methylimidazolium chloride, [EMIM]Cl (5.0 g, 34.1 mmol), in deionised water (20 ml), and the mixture is stirred for 10 min. The aqueous phase is subsequently separated off from the ionic liquid using a pipette, washed with bidistilled water (4×5 ml) and dried at 50° C. in a high vacuum. Yield of liquid 1-ethyl-3-methylimidazolium cyanodifluorotrifluoromethylborate is 5.7 g (22.4 mmol), 69%, based on the potassium cyanodifluorotrifluoromethylborate employed.

Melting point: 13° C. Water content (Karl Fischer titration): 40 ppm. Dynamic viscosity (20° C.): 16.5 mPa·s, (40° C.): 10.3 mPa·s, (60° C.) 6.9 mPa·s, (80° C.) 5.0 mPa·s.

$^1$H-NMR: δ, ppm=1.5 t (CH$_3$, 3H), $^3J_{H,H}$=7 Hz; 4.0 s (CH$_3$, 3H); 4.3 q (CH$_2$, 2H), $^3J_{H,H}$=7 Hz; 7.6 m (CH, 1H); 7.7 m (CH, 1H); 8.9 br.s (CH, 1H).

$^{13}$C{$^1$H}-NMR (cation): δ, ppm=136.8 s (1C), 124.6 s (1C), 122.9 s (1C), 45.6 s (1C), 36.5 s (1C), 15.4 s (1C).

$^{11}$B-NMR: δ, ppm=−3.8 tq (1B), $^1J_{F,B}$=49.0 Hz, $^2J_{F,B}$=34.5 Hz.

$^{19}$F-NMR: δ, ppm=−77.4 q (CF$_3$, 3F), $^2J_{F,B}$=34.5 Hz; −169.1 q (BF$_2$, 2F), $^1J_{F,B}$=49.3 Hz

Example 12

1-Ethyl-2,3-dimethylimidazolium cyanodifluorotrifluoromethylborate—[C$_7$H$_{13}$N$_2$][CF$_3$BF$_2$(CN)]

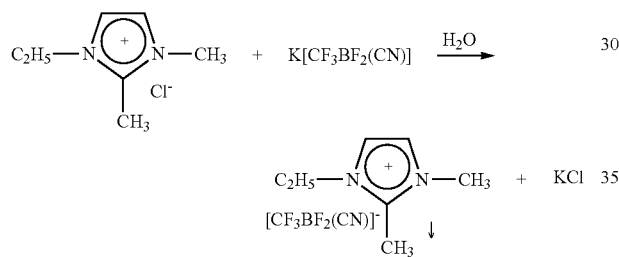

Potassium cyanodifluorotrifluoromethylborate K[CF$_3$BF$_2$(CN)] (8.0 g, 43.7 mmol) is taken up in deionised water (5 ml), and a solution of 1-ethyl-2,3-dimethylimidazolium chloride [EDMIM]Cl (7.7 g, 47.9 mmol) in 10 ml of deionised water is added. The ionic liquid obtained is washed with deionised water (4×2 ml), separated off and dried at 50° C. in vacuo for 2 days. The yield of 1-ethyl-2,3-dimethylimidazolium cyanodifluorotrifluoromethylborate is 11.2 g (39.4 mmol), 90%, based on the potassium cyanodifluorotrifluoromethylborate K[CF$_3$BF$_2$(CN)] employed. The product is analysed by means of ion chromatography and has low levels of contamination with halide; chloride: 28 ppm, fluoride: 236 ppm. Water content (Karl Fischer titration): 57 ppm. Dynamic viscosity (20° C.): 51.6 mPa·s.

Raman spectroscopy: ṽ (CN)=2209 cm$^{-1}$ $^1$H-NMR: δ, ppm=7.59 d (CH, 1H), $^3J_{H,H}$=2.15 Hz; 7.53 d (CH, 1H), $^3J_{H,H}$=2.15 Hz; 4.31 q (CH$_2$, 2H), $^3J_{H,H}$=7.30 Hz; 3.89 s (CH$_3$, 3H); 2.72 s (CH$_3$, 3H); 1.45 t (CH$_3$, 3H), $^3J_{H,H}$=7.30 Hz.

$^{13}$C{$^1$H}-NMR (cation): δ, ppm=145.37 s (C$_{tert}$, 1C); 123.34 s (CH, 1C); 121.24 s (CH, 1C); 44.30 s (CH$_2$, 1C); 35.39 s (CH$_3$, 1C); 15.21 s (CH$_3$, 1C); 9.55 s (CH$_3$, 1C).

$^{11}$B-NMR: δ, ppm=−3.8 tq (1B), $^1J_{F,B}$=49.0 Hz, $^2J_{F,B}$=34.5 Hz.

$^{19}$F-NMR: δ, ppm=−77.4 q (CF$_3$, 3F), $^2J_{F,B}$=34.5 Hz; −169.1 q (BF$_2$, 2F), $^1J_{F,B}$=49.3 Hz Elemental analysis. Found, %, C, 40.10; H, 4.93; N, 16.20; calculated for C$_7$H$_{13}$BF$_5$N$_3$, %, C, 40.18; H, 4.87; N, 15.62.

Example 13

Tetraphenylphosphonium cyanodifluorotrifluoromethylborate—[(C$_6$H$_5$)$_4$P][CF$_3$BF$_2$(CN)]

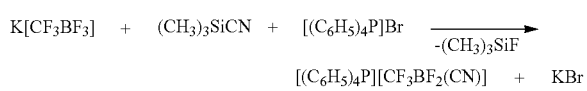

Potassium trifluorotrifluoromethylborate, K[CF$_3$BF$_3$] (0.3 g, 1.7 mmol), is introduced into a cylindrical reaction vessel with a glass valve and a PTFE spindle (Young, London) and a magnetic stirrer bar. Trimethylsilyl cyanide (5.0 ml, 37.5 mmol) is added under an argon atmosphere. The reaction mixture is stirred at room temperature for 24 hours. All volatile constituents are removed in vacuo, and most of the unreacted trimethylsilyl cyanide (4.3 ml, 32.3 mmol) is recovered by fractional distillation. The residue is dissolved in deionised water (10 ml) and precipitated using [Ph$_4$P]Br (1.2 g, 2.8 mmol) dissolved in deionised water (20 ml), filtered off and dried in vacuo. Yield of tetraphenylphosphonium cyanodifluorotrifluoromethylborate: 0.8 g (1.7 mmol), 97%, based on the potassium trifluorotrifluoromethylborate, K[CF$_3$BF$_3$], employed.

Melting point: 219° C.

$^1$H-NMR: δ, ppm=7.80-7.92 m (4C$_6$H$_5$, 16H); 7.97-8.05 m (4C$_6$H$_5$, 4H).

$^{13}$C{$^1$H}-NMR (cation): δ, ppm=136.3 s (4C), 135.6 d (8C), J$_{C,P}$=10 Hz. 131.3 d (8C), J$_{C,P}$=13 Hz, 118.9 d (4C), J$_{C,P}$=91 Hz.

$^{11}$B-NMR: δ, ppm=−3.8 tq (1B), $^1J_{F,B}$=49.0 Hz, $^2J_{F,B}$=34.5 Hz.

$^{19}$F-NMR: δ, ppm=−77.4 q (CF$_3$, 3F), $^2J_{F,B}$=34.5 Hz; −169.1 q (BF$_2$, 2F), $^1J_{F,B}$=49.3 Hz Elemental analysis. Found, %, C, 64.22; H, 4.65; N, 2.91; calculated for C$_{26}$H$_{20}$BF$_5$NP, %, C, 64.62; H, 4.17; N, 2.90.

Example 14

N-Butyl-N-methylpyrrolidinium cyanodifluorotrifluoromethylborate—[C$_9$H$_{20}$N][CF$_3$BF$_2$(CN)]

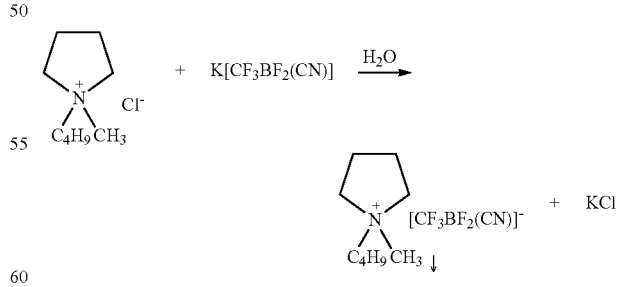

K[CF$_3$BF$_2$(CN)] (220 mg, 1.2 mmol), prepared as described in Example 2, is dissolved in deionised water (5 ml), and 1-butyl-1-methylpyrrolidinium chloride (250 mg, 1.4 mmol) is added. The ionic liquid formed is extracted with CH$_2$Cl$_2$ (2×10 ml). The dichloromethane solution is dried using MgSO$_4$, filtered, and the CH$_2$Cl$_2$ is removed using a rotary evaporator. Yield of N-butyl-N-methylpyrrolidinium cyanodifluorotrifluoromethylborate, which is liquid at room temperature, is 293 mg (1.0 mmol), 85%, based on potassium cyanodifluorotrifluoromethylborate, K[CF$_3$BF$_2$(CN)], employed.

Raman spectroscopy: $\tilde{v}$ (CN)=2208 cm$^{-1}$.

$^1$H-NMR: δ, ppm=3.68-3.75 m (2OH$_2$, 4H), 3.51-3.57 m (CH$_2$, 2H), 2.82 s (CH$_3$, 3H), 2.28-2.36 m (2CH$_2$, 4H), 1.86-1.95 m (CH$_2$, 2H), 1.44 m (CH$_2$, 2H), $^3J_{H,H}$=7 Hz; 0.98 t (CH$_3$, 3H), $^3J_{H,H}$=7 Hz.

$^{13}$C{$^1$H}-NMR (cation): δ, ppm=65.2 t (2C); 65.0 t (1C); 49.0 t (1C); 26.2 s (1C); 22.3 s (2C); 20.3 s (1C); 13.7 s (10).

$^{11}$B-NMR: δ, ppm=−3.8 tq (1B), $^1J_{F,B}$=49.0 Hz, $^2J_{F,B}$=34.5 Hz.

$^{19}$F-NMR: δ, ppm=−77.4 q (CF$_3$, 3F), $^2J_{F,B}$=34.5 Hz; −169.1 q (BF$_2$, 2F), $^1J_{F,B}$=49.3 Hz Example 15

Tetraphenylphosphonium dicyanofluorotrifluoromethylborate—[(C$_6$H$_5$)$_4$P][CF$_3$BF(CN)$_2$]

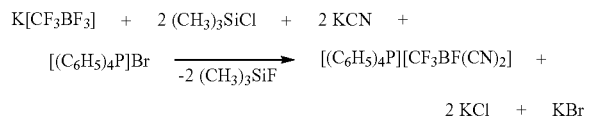

Finely ground potassium cyanide (30.1 g, 462.2 mmol) and potassium iodide (6.1 g, 36.7 mmol) are dried at 115° C. in vacuo in 5 hours in a 100 ml flask with a magnetic stirrer bar and a reflux condenser. Trimethylsilyl chloride (32.0 ml, 27.4 g, 252.2 mmol) is subsequently added, and the reaction mixture is warmed under reflux for 24 hours (60-80° C.; bath temperature). Elemental iodine (1.0 g, 3.9 mmol) is then added in a counterstream of argon, and the mixture is heated at 110° C. until reflux is no longer observed. K[CF$_3$BF$_3$] (1.6 g, 9.1 mmol) is added at room temperature, and the reaction mixture is warmed under reflux for 48 hours. All volatile constituents are subsequently removed at 100° C. in vacuo, and K$_2$CO$_3$ (2 g) is added to the residue obtained, which is then extracted with THF (4×50 ml). An aqueous potassium hydroxide solution (1.0 g, 17.8 mmol, 150 ml) is added to the combined THF phases. The THF is separated off at 70° C. using a rotary evaporator. An aqueous [Ph$_4$P]Br solution (4.5 g, 10.7 mmol, 100 ml) is slowly added to the reaction mixture. The colourless precipitate is filtered off, taken up in acetone (150 ml), and Celite is added. The mixture is filtered, and the solution is evaporated to a volume of 5 ml using a rotary evaporator. Slow addition of diethyl ether (100 ml) results in the precipitation of colourless [Ph$_4$P][CF$_3$BF(CN)$_2$]. Yield of tetraphenylphosphonium dicyanofluorotrifluoromethylborate is 2.5 g (5.1 mmol), 56%, based on the potassium trifluorotrifluoromethylborate, K[CF$_3$BF$_3$], employed.

Melting point: 150° C.; decomposition from 290° C. Raman spectroscopy: v (CN)=2215 cm$^{-1}$.

$^1$H-NMR: δ, ppm=7.8-7.92 m (4C$_6$H$_5$, 16H); 7.97-8.05 m (4C$_6$H$_5$, 4H).

$^{13}$C{$^1$H}-NMR (cation): δ, ppm=136.3 s (4C), 135.6 d (8C), $J_{C,P}$=10 Hz, 131.3 d (8C), $J_{C,P}$=13 Hz, 118.9 d (4C), $J_{C,P}$=91 Hz.

$^{11}$B-NMR: δ, ppm=−12.8 dq (1B), $^1J_{F,B}$=49.3 Hz, $^2J_{F,B}$=35.7 Hz.

$^{19}$F-NMR: δ, ppm=−74.0 qd (CF$_3$, 3F), $^2J_{F,B}$=35.7 Hz, $^3J_{F,F}$=8.3 Hz; −219.7 qq (BF, 1F), $^1J_{F,B}$=49.2 Hz, $^3J_{F,F}$=8.0 Hz.

Example 16

1-Ethyl-3-methylimidazolium dicyanofluorotrifluoromethylborate—[C$_6$H$_{11}$N$_2$][CF$_3$BF(CN)$_2$]

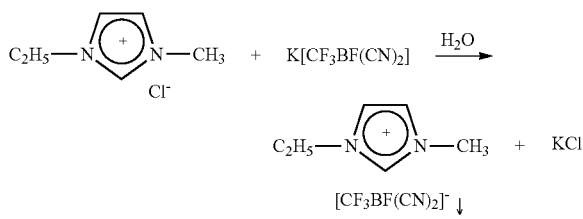

Potassium dicyanofluorotrifluoromethylborate, K[CF$_3$BF(CN)$_2$] (5.0 g, 26.3 mmol), prepared as described in Example 3, is dissolved in deionised water (15 ml), and a solution of 1-ethyl-3-methylimidazolium chloride, [EMIM]Cl (3.8 g; 26.3 mmol), in deionised water (15 ml) is added with vigorous stirring. The mixture is stirred for 10 min. The aqueous phase is subsequently removed using a pipette, and the colourless ionic liquid obtained is washed with bidistilled water (4×5 ml) and subsequently dried at 50° C. in vacuo. Yield of liquid 1-ethyl-3-methylimidazolium dicyanofluorotrifluoromethylborate is 5.5 g (21.1 mmol, 80%). Melting point: −29° C. Water content (Karl Fischer titration): 20 ppm. Dynamic viscosity (20° C.): 14.0 mPa·s, (40° C.): 8.6 mPa·s, (60° C.) 5.8 mPa·s, (80° C.) 4.2 mPa·s.

$^1$H-NMR: δ, ppm=1.5 t (CH$_3$, 3H), $^3J_{H,H}$=7 Hz; 4.0 s (CH$_3$, 3H); 4.3 q (CH$_2$, 2H), $^3J_{H,H}$=7 Hz; 7.6 m (CH, 1H); 7.7 m (CH, 1H); 8.9 br.s (CH, 1H).

$^{13}$C{$^1$H}-NMR (cation): δ, ppm=136.8 s (1C), 124.6 s (1C), 122.9 s (1C), 45.6 s (1C), 36.5 s (1C), 15.4s (1C).

$^{11}$B-NMR: δ, ppm=−12.8 dq (1B), $^1J_{F,B}$=49.3 Hz, $^2J_{F,B}$=35.7 Hz.

$^{19}$F-NMR: δ, ppm=−74.0 qd (CF$_3$, 3F), $^2J_{F,B}$=35.7 Hz, $^3J_{F,F}$=8.3 Hz; −219.7 qq (BF, 1F), $^1J_{F,B}$=49.2 Hz, $^3J_{F,F}$=8.0 Hz Example 17

1-Ethyl-3-methylimidazolium cyanodifluoropentafluoroethylborate—[C$_6$H$_{11}$N$_2$][C$_2$F$_5$BF$_2$(CN)]

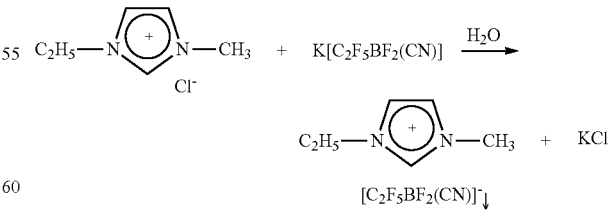

A.

Potassium cyanodifluoropentafluoroethylborate, K[C$_2$F$_5$BF$_2$(CN)] (6.9 g, 29.6 mmol), prepared as described in Example 5, and 1-ethyl-3-methylimidazolium chloride, [EMIM]Cl (4.5 g, 30.7 mmol), are taken up in a mixture of $CH_2Cl_2$ (100 ml) and deionised water (20 ml) and stirred for 1 hour. The aqueous phase is subsequently separated off, and the organic phase is washed with deionised water (5×50 ml) until the test for chloride ions using $AgNO_3$ is negative. The dichloromethane phase is dried using $MgSO_4$, filtered and evaporated at 60° C. using a rotary evaporator. The virtually colourless liquid obtained is dried at 50° C. in vacuo. The yield of liquid 1-ethyl-3-methylimidazolium cyanodifluoropentafluoroethylborate is 6.5 g (21.3 mmol), 72%, based on the potassium cyanodifluoropentafluoroethylborate, $K[C_2F_5BF_2(CN)]$, employed. Melting point: <−55° C.; decomposition from 225° C. Dynamic viscosity (20° C.): 17.6 mPa·s, (40° C.): 10.8 mPa·s, (60° C.) 7.2 mPa·s, (80° C.) 5.2 mPa·s.

Raman spectroscopy: $\tilde{v}$ (CN)=2208 $cm^{-1}$ $^1$H-NMR: δ, ppm=1.5 t ($CH_3$, 3H), $^3J_{H,H}$=7 Hz; 4.0 s ($CH_3$, 3H); 4.3 q ($CH_2$, 2H), $^3J_{H,H}$=7 Hz; 7.6 m (CH, 1H); 7.7 m (CH, 1H); 8.9 br.s (CH, 1H).

$^{13}C\{^1H\}$-NMR (cation): δ, ppm=136.8 s (1C), 124.6 s (1C), 122.9 s (1C), 45.6 s (1C), 36.5 s (1C), 15.4 s (1C).

$^{11}$B-NMR: δ, ppm=−2.7 tt (1B), $^1J_{F,B}$=51.0 Hz, $^2J_{F,B}$=25.3 Hz $^{19}$F-NMR: δ, ppm=−83.3 t ($CF_3$, 3F), $^4J_{F,F}$=5.2 Hz; -136.3 q ($CF_2$, 2F), $^2J_{F,B}$=23.3 Hz; -167.2 qq ($BF_2$, 2F), $^1J_{F,B}$=51.1 Hz, $^4J_{F,F}$=5.1 Hz Elemental analysis. Found, %, C, 35.44; H, 3.50; N, 13.81; calculated for $C_3H_{11}BF_7N_3$, %, C, 35.44; H, 3.64; N, 13.78.

B.

Potassium trifluoropentafluoroethylborate, $K[C_2F_5BF_3]$ (1.0 g, 4.42 mmol) and 1-ethyl-3-methylimidazolium chloride, [EMIM]Cl (650 mg, 4.43 mmol), are weighed out into a 10 ml reaction vessel with a glass valve and a PTFE spindle (Young, London) and a magnetic stirrer. Deionised water (1 ml) is added, and the reaction mixture is stirred for 15 minutes. The aqueous phase is separated off, and ionic liquid remaining is washed with deionised water (1 ml) and dried at 50° C. in vacuo for 4 hours. NaCN (660 mg, 13.46 mmol) and trimethylsilyl chloride, $(CH_3)_3SiCl$ (1.7 ml, 13.45 mmol), are then added, and the reaction mixture is stirred at 60° C. (oil-bath temperature) for 10 hours. The volatile constituents are removed in vacuo, the suspension obtained is washed with deionised water (3×2 ml), and the clear ionic liquid is dried at 50° C. in vacuo. The yield of liquid 1-ethyl-3-methylimidazolium cyanodifluoropentafluoroethylborate at room temperature is 1.2 g (3.93 mmol), 89%, based on the potassium trifluoropentafluoroethylborate, $K[C_2F_5BF_3]$, employed. The purity of the product is 98% according to the $^{11}$B- and $^{19}$F-NMR spectroscopic investigations.

Example 18

1-Ethyl-2,3-dimethylimidazolium cyanodifluoropentafluoroethylborate—$[C_7H_{13}N_2][C_2F_5BF_2(CN)]$

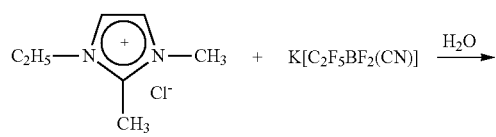

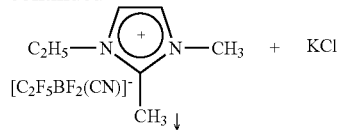

Potassium cyanodifluoropentafluoroethylborate $K[C_2F_5BF_2(CN)]$ (4.2 g, 18.0 mmol) is taken up in deionised water (2 ml), and a solution of 1-ethyl-2,3-dimethylimidazolium chloride [EDMIM]Cl (3.2 g, 19.9 mmol) in 3 ml of deionised water is added. The ionic liquid obtained is washed with deionised water (4×2 ml), separated off and dried at 50° C. in vacuo. The yield of 1-ethyl-2,3-dimethylimidazolium cyanodifluoropentafluoroethylborate, which is liquid at room temperature, is 5.1 g (15.9 mmol), 88%, based on the potassium cyanodifluoropentafluoroethylborate $K[C_2F_5BF_2(CN)]$ employed. The product is analysed by means of ion chromatography and has low levels of contamination with halide; chloride: 7 ppm, bromide: 16 ppm, fluoride: 14 ppm. Water content (Karl Fischer titration): 161 ppm. Dynamic viscosity (20° C.): 47.2 mPa·s.

Raman spectroscopy: $\tilde{v}$ (CN)=2209 $cm^{-1}$ $^1$H-NMR: δ, ppm=7.60 d (CH, 1H), $^3J_{H,H}$=2.15 Hz; 7.55 d (CH, 1H), $^3J_{H,H}$=2.15 Hz; 4.32 q ($CH_2$, 2H), $^3J_{H,H}$=7.30 Hz; 3.90 s ($CH_3$, 3H); 2.75 s ($CH_3$, 3H); 1.46 t ($CH_3$, 3H), $^3J_{H,H}$=7.30 Hz.

$^{13}C\{^1H\}$-NMR (cation): δ, ppm=145.32 s ($C_{tert}$, 1C); 123.30 s (CH, 1C); 121.19 s (CH, 1C); 44.20 s ($CH_2$, 1C); 35.35 s ($CH_3$, 1C); 15.07 s ($CH_3$, 1C); 9.46 s ($CH_3$, 1C).

$^{11}$B-NMR: δ, ppm=−2.7 tt (1B), $^1J_{F,B}$=51.0 Hz, $^2J_{F,B}$=25.3 Hz.

$^{19}$F-NMR: δ, ppm=−83.3 t ($CF_3$, 3F), $^4J_{F,F}$=5.2 Hz; -136.3 q ($CF_2$, 2F), $^2J_{F,B}$=23.3 Hz; -167.2 qq ($BF_2$, 2F), $^1J_{F,B}$=51.1 Hz, $^4J_{F,F}$=5.1 Hz Elemental analysis. Found, %, C, 37.57; H, 3.84; N, 13.10; calculated for $C_{10}H_{13}BF_7N_3$, %, C, 37.65; H, 4.11; N, 13.17.

Example 19

1-Butyl-3-methylimidazolium cyanodifluoropentafluoroethylborate—$[C_8H_{15}N_2][C_2F_5BF_2(CN)]$ Potassium cyanodifluoropentafluoroethylborate $K[C_2F_5BF_2(CN)]$ (4.0 g, 17.1 mmol), prepared as described in Example 5, is dissolved in deionised water (2 ml), and a solution of 1-butyl-3-methylimidazolium chloride [BMIM]Cl (3.4 g, 19.4 mmol) in 3 ml of deionised water is added. The ionic liquid obtained is washed with deionised water (4×2 ml), separated off and dried at 50° C. in vacuo. The yield of 1-butyl-3-methylimidazolium cyanodifluoropentafluoroethylborate, which is liquid at room temperature, is 5.2 g (15.6 mmol), 91%, based on the potassium cyanodifluoropentafluoroethylborate $K[C_2F_5BF_2(CN)]$ employed. The product is analysed by means of ion chromatography and has low levels of contamination with halide; chloride: <5 ppm, bromide: 5 ppm, fluoride: 22 ppm. Water content (Karl Fischer titration): 25 ppm. Dynamic viscosity (20° C.): 27.4 mPa·s.

Raman spectroscopy: $\tilde{v}$ (CN)=2209 cm$^{-1}$ $^1$H-NMR: δ, ppm=8.95 d,d (CH, 1H) $^4J_{H,H}$≈1.6 Hz; 7.69 d,d (CH, 1H), $^3J_{H,H}$≈$^4J_{H,H}$≈1.7 Hz; 7.65 d,d (CH, 1H) $^3J_{H,H}$≈$^4J_{H,H}$≈1.7 Hz; 4.34 t (CH$_2$, 2H), J$_{H,H}$=7.33 Hz; 4.02 s (CH$_3$, 3H); 1.92 m (CH$_2$, 2H); 1.39 m (CH$_2$, 2H); 0.92 t (CH$_3$, 3H), J$_{H,H}$=7.37 Hz.

$^{13}$C{$^1$H}-NMR (cation): δ, ppm=137.40 s (CH, 1C); 124.86 s (CH, 1C);

123.47 s (CH, 1C); 50.30 s (CH$_2$, 1C); 36.68 s (CH$_3$, 1C); 32.59 s (CH$_2$, 1C); 19.98 s (CH$_2$, 1C); 13.50 s (CH$_3$, 1C).

$^{11}$B-NMR: δ, ppm=−2.7 tt (1B), $^1J_{F,B}$=51.0 Hz, $^2J_{F,B}$=25.3 Hz.

$^{19}$F-NMR: δ, ppm=−83.3 t (CF$_3$, 3F), $^4J_{F,F}$=5.2 Hz; −136.3 q (CF$_2$, 2F), $^2J_{F,B}$=23.3 Hz; −167.2 qq (BF$_2$, 2F), $^1J_{F,B}$=51.1 Hz, $^4J_{F,F}$=5.1 Hz.

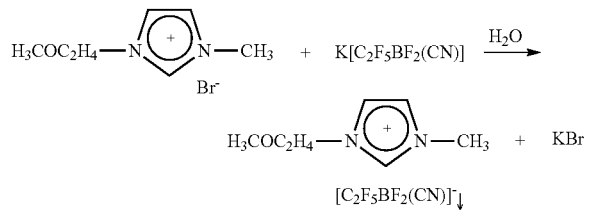

Elemental analysis. Found, %, C, 39.60; H, 4.56; N, 12.64; calculated for C$_{11}$H$_{15}$BF$_7$N$_3$, %, C, 39.67; H, 4.54; N, 12.62.

Example 20

1-(2-Methoxyethyl)-3-methylimidazolium cyanodifluoropentafluoroethylborate—[C$_7$H$_{13}$N$_2$O][C$_2$F$_5$BF$_2$(CN)]

A solution of 1-(2-methoxyethyl)-3-methylimidazolium bromide [MOEMIM]Br (4.7 g, 21.2 mmol) in 3 ml of deionised water is added to a solution of potassium cyanodifluoropentafluoroethylborate K[C$_2$F$_5$BF$_2$(CN)] (4.5 g, 19.3 mmol) in 2 ml of deionised water. The ionic liquid obtained is washed with deionised water (4×2 ml), separated off and dried at 60° C. in vacuo. The yield of 1-methoxyethyl-3-methylimidazolium cyanodifluoropentafluoroethylborate is 5.7 g (17.0 mmol), 88%, based on the potassium cyanodifluoropentafluoroethylborate K[C$_2$F$_5$BF$_2$(CN)] employed. The product is analysed by means of ion chromatography and has low levels of contamination with halide; bromide: <5 ppm, chloride: <5 ppm, fluoride: 23 ppm. Water content (Karl Fischer titration): 215 ppm. Dynamic viscosity (20° C.):27.1 mPa·s.

Raman spectroscopy: $\tilde{v}$ (CN)=2210 cm$^{-1}$ $^1$H-NMR: δ, ppm=8.95 d,d (CH, 1H), $^4J_{F,F}$≈1.7 Hz; 7.68 d,d (CH, 1H), $^3J_{H,H}$≈$^4J_{H,H}$≈1.7 Hz; 7.67 d,d (CH, 1H), $^3J_{H,H}$≈$^4J_{H,H}$≈1.7 Hz; 4.51 m (CH$_2$, 2H); 4.09 s (CH$_3$, 3H); 3.82 m (CH$_2$, 2H); 3.34 s (CH$_3$, 3H).

$^{13}$C{$^1$H}-NMR (cation): δ, ppm=137.69 s (CH, 1C); 124.43 s (CH, 1C); 123.88 s (CH, 1C); 70.68 s (CH$_2$, 1C); 58.83 s (CH$_3$, 1C); 50.42 s (CH$_2$, 1C); 36.61 s (CH$_3$, 1C).

$^{11}$B-NMR: δ, ppm=−2.7 tt (1B), $^1J_{F,B}$=51.0 Hz, $^2J_{F,B}$=25.3 Hz.

$^{19}$F-NMR: δ, ppm=−83.3 t (CF$_3$, 3F), $^4J_{F,F}$=5.2 Hz; −136.3 q (CF$_2$, 2F), $^2J_{F,B}$=23.3 Hz; −167.2 qq (BF$_2$, 2F), $^1J_{F,B}$=51.1 Hz, $^4J_{F,F}$=5.1 Hz.

Elemental analysis. Found, %, C, 35.13; H, 4.03; N, 12.58; calculated for C$_{10}$H$_{13}$BF$_7$N$_3$O, %, C, 35.85; H, 3.91; N, 12.54.

Example 21

Tetra-n-butylammonium cyanodifluoropentafluoroethylborate—[(n-C$_4$H$_9$)$_4$N][C$_2$F$_5$BF$_2$(CN)]

A.

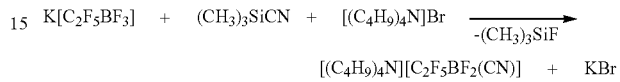

Potassium trifluoropentafluoroethylborate, K[C$_2$F$_5$BF$_3$] (1.0 g, 4.4 mmol), is weighed out into a cylindrical reaction vessel with a glass valve and a PTFE spindle (Young, London). The flask is evacuated, and a mixture of trimethylsilyl cyanide (25.0 ml, 187.5 mmol) and acetonitrile (6 ml) is added in a counterstream of argon. A reflux condenser is attached in the counterstream of argon, and the reaction mixture is irradiated in a microwave (CEM Discover) (100 W, T$_{max}$=75° C.) for 10 min. All volatile constituents are removed in vacuo, and most of the unreacted trimethylsilyl cyanide (21.5 ml, 161.1 mmol) is recovered by fractional distillation. The residue is dissolved in deionised water (10 ml). Virtually colourless [n-Bu$_4$N]—[C$_2$F$_5$BF$_2$CN] is precipitated by addition of an aqueous solution of [n-Bu$_4$N]Br (2.5 g; 7.8 mmol) in deionised water (20 ml). The yield of tetra-n-butylammonium cyanodifluoropentafluoroethylborate is 1.8 g (4.1 mmol), 93%, based on the potassium trifluoropentafluoroethylborate, K[C$_2$F$_5$BF$_3$], employed. Melting point: 80° C.; decomposition from 250° C.

$^1$H-NMR: δ, ppm=1.0 t (4CH$_3$, 12H), $^3J_{H,H}$=7 Hz; 1.4 m (4CH$_2$, 8H), $^3J_{H,H}$=7 Hz, 1.7-1.8 m (4-CH$_2$, 8H); 3.3-3.5 m, (4-CH$_2$, 8H).

$^{13}$C{$^1$H}-NMR (cation): δ, ppm=59.3 s (4C), 24.3 s (4C), 20.2 s (4C), 13.7 (4C).

$^{11}$B-NMR: δ, ppm=−2.7 tt (1B), $^1J_{H,B}$=51.0 Hz, $^2J_{F,B}$=25.3 Hz.

$^{19}$F-NMR: δ, ppm=−83.3 t (CF$_3$, 3F), $^4J_{F,F}$=5.2 Hz; −136.3 q (CF$_2$, 2F), $^2J_{F,B}$=23.3 Hz; −167.2 qq (BF$_2$, 2F), $^1J_{F,B}$=51.1 Hz, $^4J_{F,F}$=5.1 Hz.

B.

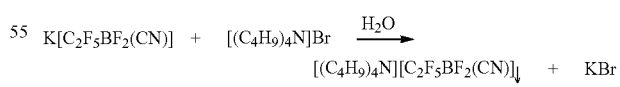

Potassium cyanodifluoropentafluoroethylborate, K[C$_2$F$_5$BF$_2$CN] (0.5 g, 2.1 mmol), prepared as described in Example 5, is dissolved in deionised water (50 ml), and an aqueous solution of [n-Bu$_4$N]Br (1.4 g, 4.3 mmol, 100 ml) is added with stirring. After 15 min, the colourless precipitate is filtered off and dried in vacuo. The yield of tetra-n-butylammonium cyanodifluoropentafluoroethylborate is 0.84 g (1.9 mmol), 90%, based on the potassium cyanodifluoropentafluoroethylborate, K[C₂F₅BF₂CN], employed. ¹H and ¹³C NMR spectra correspond to the values indicated in Example 21,A.

Example 22

Tributylmethylammonium cyanodifluoropentafluoroethylborate—[(C₄H₉)₃CH₃N][C₂F₅BF₂(CN)]

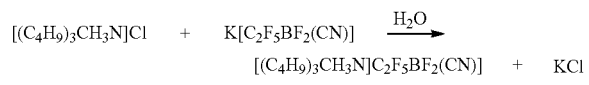

Tributylmethylammonium chloride [(C₄H₉)₃CH₃N]Cl (4.3 g, 18.2 mmol), dissolved in 4 ml of deionised water, is added to an aqueous solution (4 ml) of potassium cyanodifluoropentafluoroethylborate K[C₂F₅BF₂(CN)] (3.8 g, 16.3 mmol). The ionic liquid formed is washed with deionised water (4×2 ml), separated off and dried at 60° C. in vacuo. The yield of tributylmethylammonium cyanodifluoropentafluoroethylborate is 5.7 g (14.4 mmol), 88%, based on the potassium cyanodifluoropentafluoroethylborate K[C₂F₅BF₂(CN)] employed. The product is analysed by means of ion chromatography and has low levels of contamination with halide; chloride: 14 ppm, bromide: 9, fluoride: 19 ppm. Water content (Karl Fischer titration): 142 ppm. Dynamic viscosity (20° C.): 216.7 mPa·s.

Raman spectroscopy: ṽ (CN)=2208 cm⁻¹

¹H-NMR: δ, ppm=3.38 m (3CH₂, 6H); 3.10 s (CH₃, 3H); 1.78 m (3CH₂, 6H); 1.39 m (3CH₂, 6H); 0.95 t (CH₃, 9H), ³J$_{H,H}$=7.39 Hz.

¹³C{¹H}-NMR (cation): δ, ppm=62.31 s (CH₂, 3C); 48.69 s (CH₃, 1C); 24.63 s (CH₂, 3C); 20.15 s (CH₂, 3C); 13.65 s (CH₃, 3C).

¹¹B-NMR: δ, ppm=−2.7 tt (1B), ¹J$_{F,B}$=51.0 Hz, ²J$_{F,B}$=25.3 Hz.

¹⁹F-NMR: δ, ppm=−83.3 t (CF₃, 3F), ⁴J$_{F,F}$=5.2 Hz; −136.3 q (CF₂, 2F), ²J$_{F,B}$=23.3 Hz; −167.2 qq (BF₂, 2F), ¹J$_{F,B}$=51.1 Hz, ⁴J$_{F,F}$=5.1 Hz Elemental analysis. Found, %, C, 48.79; H, 7.81; N, 7.21; calculated for C₁₆H₃₀BF₇N₂, %, C, 48.75; H, 7.67; N, 7.11.

Example 23

N-Butyl-N-methylpyrrolidinium cyanodifluoropentafluoroethylborate—[C₉H₂₀N][C₂F₅BF₂(CN)]

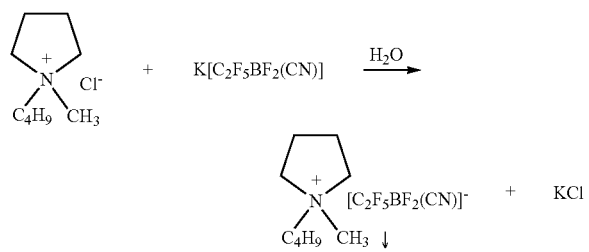

A. Potassium cyanodifluoropentafluoroethylborate K[C₂F₅BF₂(CN)] (4.2 g, 18.0 mmol) and N-butyl-N-methylpyrrolidinium chloride [BMPL] (3.5 g, 19.6 mmol) are each dissolved in 2 ml of deionised water. The solutions are combined, and the ionic liquid obtained is washed with deionised water (4×2 ml). The colourless liquid is dried at 60° C. in vacuo. The yield of N-butyl-N-methylpyrrolidinium cyanodifluoropentafluoroethylborate, which is liquid at room temperature, is 5.9 g (17.5 mmol), 97%, based on the potassium cyanodifluoropentafluoroethylborate K[C₂F₅BF₂(CN)] employed. The product is analysed by means of ion chromatography and has low levels of contamination with halide; chloride: 8 ppm, bromide: 6 ppm, fluoride: 29 ppm. Water content (Karl Fischer titration): 21 ppm. Dynamic viscosity (20° C.): 43.2 mPa·s.

Raman spectroscopy: ṽ (CN)=2208 cm⁻¹

¹H-NMR: δ=3.59 m (2CH₂, 4H); 3.42 m (CH₂, 2H); 2.79 s (CH₃, 3H); 2.30 m (2CH₂, 4H); 1.85 m (CH₂, 2H); 1.40 m (CH₂, 2H); 0.97 ppm t (CH₃, 3H), ³J$_{H,H}$=7.37 Hz.

¹³C{¹H}(cation): δ=65.10 s (CH₂, 2C); 64.89 s (CH₂, 1C); 48.92 s (CH₃, 1C); 26.11 s (CH₂, 1C); 22.20 s (CH₂, 2C); 20.21 s (CH₂, 1C); 13.51 s (CH₃, 1C)

¹¹B-NMR: δ, ppm=−2.7 tt (1B), ¹J$_{F,B}$=51.0 Hz, ²J$_{F,B}$=25.3 Hz.

¹⁹F-NMR: δ, ppm=−83.3 t (CF₃, 3F), ⁴J$_{F,F}$=5.2 Hz; −136.3 q (CF₂, 2F), ²J$_{F,B}$=23.3 Hz; −167.2 qq (BF₂, 2F), ¹J$_{F,B}$=51.1 Hz, ⁴J$_{F,F}$=5.1 Hz.

Elemental analysis. Found, %, C, 42.90; H, 5.99; N, 8.32; calculated for C₁₂H₂₀BF₇N₂, %, C, 42.88; H, 6.00; N, 8.33.

B. Potassium trifluoropentafluoroethylborate, K[C₂F₅BF₃] (1.0 g, 4.4 mmol), and N-butyl-N-methylpyrrolidinium chloride [BMPL] (865 mg, 4.9 mmol) are taken up together in deionised water (1 ml). The suspension is stirred for 15 minutes. The aqueous phase is subsequently removed, and the ionic liquid remaining is washed with deionised water (1 ml). The ionic liquid is dried at 50° C. in vacuo for 2 hours. NaCN (660 mg, 13.5 mmol) is then added, and the suspension is dried at 50° C. in vacuo for 15 minutes. Trimethylsilyl chloride (1.7 ml, 13.5 mmol) is subsequently added, and the reaction mixture is stirred at 60° C. for 24 hours. The volatile constituents are removed in vacuo, and the suspension remaining is taken up in acetone (10 ml), filtered (D4), and the acetone phase is evaporated in vacuo.

Yield: 1.2 g (3.6 mmol, 81%).

¹H, ¹⁹F and ¹¹B NMR spectra correspond to the values indicated in Example 23,A.

Example 24

Tetraphenylphosphonium cyanodifluoropentafluoroethylborate—[(C₅H₆)₄P][C₂F₅BF₂(CN)]

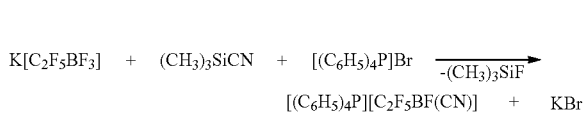

Potassium trifluoropentafluoroethylborate, K[C₂F₅BF₃] (495 mg, 2.2 mmol), is weighed out into a cylindrical reaction vessel with a glass valve and a PTFE spindle (Young, London) and a magnetic stirrer bar. Trimethylsilyl cyanide (7.0 ml; 52.5 mmol) is condensed in under an argon atmosphere. The reaction mixture is stirred at 100° C. for 5 hour. All volatile constituents are subsequently removed in vacuo. Most of the unreacted trimethylsilyl cyanide (6.1 ml, 45.7 mmol) is recovered by fractional distillation. The residue is dissolved in deionised water (15 ml), and [Ph₄P]Br (1.3 g; 3.1 mmol) dissolved in deionised water (150 ml) is added. The precipitate is filtered off and dried in vacuo. The yield of solid colourless tetraphenylphosphonium cyanodifluoropentafluoroethylborate is 1.1 g (2.0 mmol), 93%, based on the potassium trifluoropentafluoroethylborate, K[C$_2$F$_5$BF$_3$], employed. Melting point: 130° C.; decomposition from 310° C. Raman spectroscopy: $\tilde{\nu}$ (CN)=2211 cm$^{-1}$.

$^1$H-NMR: δ, ppm=7.8-7.92 m (4C$_6$H$_5$, 16H); 7.97-8.05 m (4C$_6$H$_5$, 4H).

$^{13}$C{$^1$H}-NMR (cation): δ, ppm=136.3 s (4C), 135.6 d (8C), J$_{C,F}$=10 Hz, d (8C), J$_{C,F}$=13 Hz, 118.9 d (4C), J$_{C,F}$=91 Hz.

$^{11}$B-NMR: δ, ppm=−2.7 tt (1B), $^1$J$_{F,B}$=51.0 Hz, $^2$J$_{F,B}$=25.3 Hz.

$^{19}$F-NMR: δ, ppm=−83.3 t (CF$_3$, 3F), $^4$J$_{F,F}$=5.2 Hz; -136.3 q (CF$_2$, 2F), $^2$J$_{F,B}$=23.3 Hz; -167.2 qq (BF$_2$, 2F), $^1$J$_{F,B}$=51.1 Hz, $^4$J$_{F,F}$=5.1 Hz.

Example 25

Tributylmethylphosphonium cyanodifluoropentafluoroethylborate—[(C$_4$H$_9$)$_3$CH$_3$P][C$_2$F$_5$BF$_2$(CN)]

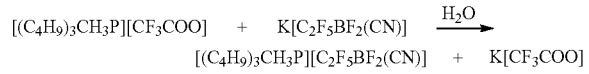

Potassium cyanodifluoropentafluoroethylborate K[C$_2$F$_5$BF$_2$(CN)] (2.6 g, 11.1 mmol) is dissolved in 2 ml of deionised water a solution of tributylmethylphosphonium trifluoroacetate [(C$_4$H$_9$)$_3$CH$_3$P][CF$_3$CO$_2$] (3.7 g, 11.1 mmol) in 3 ml of deionised water is added. The ionic liquid is washed with deionised water (4×2 ml), separated off and dried at 50° C. in vacuo. The yield of tributylmethylphosphonium cyanodifluoropentafluoroethylborate is 4.0 g (9.7 mmol), 87%, based on the potassium cyanodifluoropentafluoroethylborate K[C$_2$F$_5$BF$_2$(CN)] employed. The product is analysed by means of ion chromatography and has low levels of contamination with halide; chloride: 8 ppm, fluoride: 8 ppm. Water content (Karl Fischer titration): 129 ppm.

Raman spectroscopy: $\tilde{\nu}$ (CN)=2208 cm$^{-1}$ $^1$H-NMR: δ, ppm=2.37 m (3CH$_2$, 6H); 2.00 d (CH$_3$, 3H), $^2$J$_{P,H}$=13.8 Hz; 1.67 m (3CH$_2$, 6H); 1.50 m (3CH$_2$, 6H); 0.94 t (3CH$_3$, 9H), $^3$J$_{H,H}$=7.37 Hz.

$^{13}$C{$^1$H}-NMR (cation): δ, ppm=24.48 d (3CH$_2$, 3C), $^3$J$_{P,C}$=16.01 Hz; 23.90 d (3CH$_2$, 3C) $^2$J$_{P,C}$=4.53 Hz; 20.53 d (3CH$_2$, 3C), $^1$J$_{P,C}$=49.74 Hz; 13.55 d (3CH$_3$, 3C), $^4$J$_{P,C}$=0.85 Hz; 4.08 d (CH$_3$, 1C), $^1$J$_{P,C}$=52.88 Hz.

$^{11}$B-NMR: δ, ppm=−2.7 tt (1B), $^1$J$_{F,B}$=51.0 Hz, $^2$J$_{F,B}$=25.3 Hz.

$^{19}$F-NMR: δ, ppm=−83.3 t (CF$_3$, 3F), $^4$J$_{F,F}$=5.2 Hz; -136.3 q (CF$_2$, 2F), $^2$J$_{F,B}$=23.3 Hz; -167.2 qq (BF$_2$, 2F), $^1$J$_{F,B}$=51.1 Hz, $^4$J$_{F,F}$=5.1 Hz.

$^{31}$P{$^1$H}-NMR: δ, ppm=32.2 s.

Elemental analysis. Found, %, C, 46.61; H, 7.46; N, 3.38; calculated for C$_{16}$H$_{30}$BF$_7$N$_P$, %, C, 46.74; H, 7.35; N, 3.41.

Example 26

Diethylmethylsulfonium cyanodifluoropentafluoroethylborate—[(C$_2$H$_5$)$_2$CH$_3$S][C$_2$F$_5$BF$_2$(CN)]

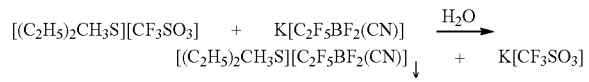

Potassium cyanodifluoropentafluoroethylborate K[C$_2$F$_5$BF$_2$(CN)] (5.2 g, 22.3 mmol), prepared as described in Example 5, is dissolved in deionised water (2 ml), and an aqueous diethylmethylsulfonium trifluoromethylsulfonate solution (6.3 g, 24.8 mmol, 3 ml) is added. The ionic liquid formed is washed with deionised water (6×2 ml) and subsequently dried at room temperature in a high vacuum for 12 hours and then at 60° C. for 24 hours. The yield of diethylmethylsulfonium cyanodifluoropentafluoroethylborate is 5.5 g (18.4 mmol), 82%, based on the potassium cyanodifluoropentafluoroethylborate K[C$_2$F$_5$BF$_2$(CN)] employed. The product is analysed by means of ion chromatography and has low levels of contamination with halide; bromide: <5 ppm, chloride: <5 ppm, fluoride: 31 ppm. Water content (Karl Fischer titration): 94 ppm. Dynamic viscosity (20° C.): 22.2 mPa·s.

Raman spectroscopy: $\tilde{\nu}$ (CN)=2209 cm$^{-1}$ $^1$H-NMR: δ, ppm=3.48 m (2CH$_2$, 4H); 3.02 s (CH$_3$, 3H); 1.52 t (2CH$_3$, 6H), $^3$J$_{H,H}$=7.44 Hz.

$^{13}$C{$^1$H}-NMR (cation): δ, ppm=35.98 s (2CH$_2$, 2C); 21.42 s (CH$_3$, 1C); 8.75 s (2CH$_3$, 2C).

$^{11}$B-NMR: δ, ppm=−2.7 tt (1B), $^1$J$_{F,B}$=51.0 Hz, $^2$J$_{F,B}$=25.3 Hz.

$^{19}$F-NMR: δ, ppm=−83.3 t (CF$_3$, 3F), $^4$J$_{F,F}$=5.2 Hz; -136.3 q (CF$_2$, 2F), $^2$J$_{F,B}$=23.3 Hz; -167.2 qq (BF$_2$, 2F), $^1$J$_{F,B}$=51.1 Hz, $^4$J$_{F,F}$=5.1 Hz.

Elemental analysis. Found, %, C, 32.14; H, 4.30; N, 4.87, S 10.71; calculated for C$_8$H$_{13}$BF$_7$NS, %, C, 32.13; H, 4.38; N, 4.68, S 10.72.

Example 27

S-Ethyl-N,N,N',N'-tetramethylisothiouronium cyanodifluoropentafluoroethylborate—[{(CH$_3$)$_2$N}$_2$CSC$_2$H$_5$][C$_2$F$_5$BF$_2$(CN)]

[{(CH$_3$)$_2$N}$_2$CSC$_2$H$_5$]I + K[C$_2$F$_5$BF$_2$(CN)] $\xrightarrow{H_2O}$ [{(CH$_3$)$_2$N}$_2$CSC$_2$H$_5$][C$_2$F$_5$BF$_2$(CN)] + KI Potassium cyanodifluoropentafluoroethylborate K[C$_2$F$_5$BF$_2$(CN)] (6.0 g, 25.7 mmol) is dissolved in 10 ml of deionised water, and a solution of S-ethyl-N,N,N',N'-tetramethylisothiouronium iodide [{(CH$_3$)$_2$N}$_2$CSC$_2$H$_5$]I (8.2 g, 28.4 mmol) in 10 ml of deionised water is added with stirring. The black liquid obtained is separated off, washed with deionised water (4×2 ml) and then dried at room temperature in vacuo for 3 days. The crude product is dissolved in CH$_2$Cl$_2$ (100 ml) and stirred slowly with active carbon (5 g) for 12 hours. The mixture is filtered, and the dichloromethane is removed using a rotary evaporator. The amber-coloured ionic liquid is dried at 50° C. in a high vacuum for 2 days. The yield of S-ethyl-N,N,N',N'-tetramethylisothiouronium cyanodifluoropentafluoroethylborate is 7.2 g (20.2 mmol), 78%, based on the potassium cyanodifluoropentafluoroethylborate K[C$_2$F$_5$BF$_2$(CN)] employed. The product is analysed by means of ion chromatography and has low levels of contamination with halide; chloride: 12 ppm, fluoride: 121 ppm. Water content (Karl Fischer titration): 20 ppm. Dynamic viscosity (20° C.): 40.2 mPa·s.

Raman spectroscopy: $\tilde{\nu}$ (CN)=2208 cm$^{-1}$ $^1$H-NMR: δ, ppm=3.45 s (4CH$_3$, 12H); 3.20 q (CH$_2$, 2H), $^3$J$_{H,H}$=7.39 Hz; 1.38 t (CH$_3$, 3H), $^3$J$_{H,H}$=7.39 Hz.

$^{13}C\{^1H\}$-NMR (cation): δ, ppm=176.58 s (C=S, 1C); 44.19 s (4CH$_3$, 4C); 29.62 s (CH$_2$, 1C); 14.98 s (CH$_3$, 1C).

$^{11}$B-NMR: δ, ppm=−2.7 tt (1B), $^1J_{F,B}$=51.0 Hz, $^2J_{F,B}$=25.3 Hz.

$^{19}$F-NMR: δ, ppm=−83.3 t (CF$_3$, 3F), $^4J_{F,F}$=5.2 Hz; -136.3 q (CF$_2$, 2F), $^2J_{F,B}$=23.3 Hz; -167.2 qq (BF$_2$, 2F), $^1J_{F,B}$=51.1 Hz, $^4J_{F,F}$=5.1 Hz.

Elemental analysis. Found, %, C, 33.91; H, 4.82; N, 12.35, S 9.73; calculated for C$_{10}$H$_{17}$BF$_7$N$_3$S, %, C, 33.82; H, 4.83; N, 11.83, S 9.03.

Example 28

Tetraphenylphosphonium dicyanofluoropentafluoro-ethylborate—[(C$_5$H$_6$)$_4$P][C$_2$F$_5$BF(CN)$_2$]

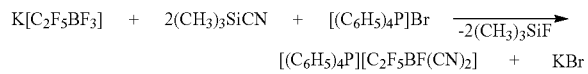

A solution of potassium trifluoropentafluoroethylborate, K[C$_2$F$_5$BF$_3$] (50 mg, 0.22 mmol), in trimethylsilyl cyanide (0.7 ml, 5.2 mmol) is heated successively at 70° C. for 7 hours, at 100° C. for 5 hours, at 125° C. for 7.5 hours, at 140° C. for 5 hours and then at 150° C. for 72 hours in an NMR tube with a glass valve and a PTFE spindle (Young, London). The solution is evaporated in vacuo, and the residue is taken up in alkaline aqueous solution (0.1 g of KOH, 10 ml), and [Ph$_4$P]Br (0.5 g, 1.2 mmol), dissolved in deionised water (50 ml), is added dropwise. The colourless precipitate formed is filtered off and dried in vacuo. The yield of tetraphenylphosphonium dicyanofluoropentafluoroethylborate is 85 mg (0.16 mmol), 73%, based on the potassium trifluoropentafluoroethylborate, K[C$_2$F$_5$BF$_3$], employed. Melting point: 103° C.

$^1$H-NMR: δ, ppm=7.8-7.92 m (4C$_6$H$_5$, 16H); 7.97-8.05 m (4C$_6$H$_5$, 4H).

$^{13}C\{^1H\}$-NMR (cation): δ, ppm=136.3 s (4C), 135.6 d (8C), $J_{C,P}$=10 Hz, d (8C), $J_{C,P}$=13 Hz, 118.9 d (4C), $J_{C,P}$=91 Hz.

$^{11}$B-NMR: δ, ppm=−12.0 d, t (1B), $^1J_{F,B}$=51.6 Hz, $^2J_{F,B}$=25.2 Hz.

$^{19}$F-NMR: δ, ppm=−82.6 d, t (CF$_3$, 3F), $^3J_{F,F}$=1.0 Hz, $^4J_{F,F}$=6.3 Hz; -132.0 q,d (CF$_2$, 2F), $^3J_{F,F}$=5.0 Hz, $^2J_{F,B}$=25.3 Hz; -219.1 q, q, t (BF, 1F), $^1J_F$, B=52 Hz, $^3J_{F,F}$=5-6 Hz, $^4J_{F,F}$=5-6 Hz.

Example 29

1-Ethyl-3-methylimidazolium dicyanofluoropen-tafluoroethylborate—[C$_6$H$_{11}$N$_2$][C$_2$F$_5$BF(CN)$_2$]

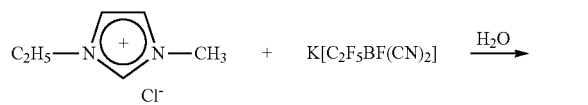

Potassium dicyanofluoropentafluoroethylborate, K[C$_2$F$_5$BF(CN)$_2$] (7.0 g, 29.2 mmol), prepared as described in Example 6, and 1-ethyl-3-methylimidazolium chloride, [EMIM]Cl (5.0 g, 34.1 mmol), are taken up in bidistilled water (15 ml) and stirred. The aqueous phase is subsequently separated off, the ionic liquid is washed with bidistilled water (4×5 ml), separated off and subsequently dried at 50° C. in a high vacuum. Yield virtually colourless liquid 1-ethyl-3-methylimidazolium dicyanofluoropentafluoroethylborate is 6.4 g (20.5 mmol), 70%, based on the potassium dicyanofluoropentafluoroethylborate, K[C$_2$F$_5$BF(CN)$_2$], employed. Melting point: −48° C. Water content (Karl Fischer titration): 6 ppm. Dynamic viscosity (20° C.): 16.4 mPa·s, (40° C.): 9.8 mPa·s, (60° C.) 6.5 mPa·s, (80° C.) 4.6 mPa·s.

$^1$H-NMR: δ, ppm=1.5 t (CH$_3$, 3H), $^3J_{H,H}$=7 Hz; 4.0 s (CH$_3$, 3H); 4.3 q (CH$_2$, 2H), $^3J_{H,H}$=7 Hz; 7.63 s (CH, 1H); 7.70 s (CH, 1H); 8.9 s (CH, 1H).

$^{13}C\{^1H\}$-NMR (cation): δ, ppm=136.8 s (1C), 124.6 s (1C), 122.9 s (1C), 45.6 s (1C), 36.5 s (1C), 15.4 s (1C).

$^{11}$B-NMR: δ, ppm=−12.0 d, t (1B), $^1J_{F,B}$=51.6 Hz, $^2J_{F,B}$=25.2 Hz.

$^{19}$F-NMR: δ, ppm=−82.6 d, t (CF$_3$, 3F), $^3J_{F,F}$=1.0 Hz, $^4J_{F,F}$=6.3 Hz; -132.0 q,d (CF$_2$, 2F), $^3J_{F,F}$=5.0 Hz, $^2J_{F,B}$=25.3 Hz; -219.1 q, q, t (BF, 1F), $^1J_{F,B}$=52 Hz, $^3J_{F,F}$=5-6 Hz, $^4J_{F,F}$=5-6 Hz.

Example 30

1-Butyl-3-methylimidazolium dicyanofluoropen-tafluoroethylborate—[C$_8$H$_{15}$N$_2$][C$_2$F$_5$BF(CN)$_2$]

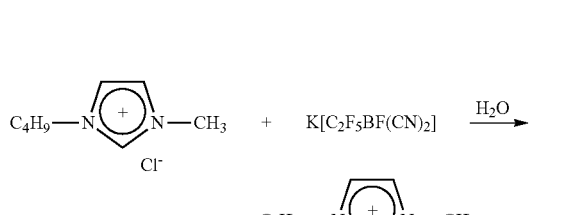

Potassium dicyanofluoropentafluoroethylborate K[C$_2$F$_5$BF(CN)$_2$] (5.0 g, 20.8 mmol), prepared as described in Example 6, and 1-butyl-3-methylimidazolium chloride [BMIM]Cl (4.0 g, 22.9 mmol) are each dissolved in 2 ml of deionised water. The two solutions are combined, and the ionic liquid formed is separated off and subsequently washed with deionised water (4×2 ml) and separated off. The virtually colourless liquid obtained is dried at 60° C. in vacuo. The yield of 1-butyl-3-methylimidazolium dicyanofluoropentafluoroethylborate is 6.5 g (19.1 mmol), 92%, based on the potassium dicyanofluoropentafluoroethylborate K[C$_2$F$_5$BF(CN)$_2$] employed. The product is analysed by means of ion chromatography and has low levels of contamination with halide; chloride: 10 ppm, fluoride: 6 ppm. Water content (Karl Fischer titration): 154 ppm. Dynamic viscosity (20° C.): 25.1 mPa·s.

Raman spectroscopy: ṽ (CN)=2215 cm$^{-1}$ $^1$H-NMR: δ, ppm=8.96 d,d (CH, 1H), $^4J_{H,H}$≈1.6 Hz; 7.70 d,d (CH, 1H), $^3J_{H,H}$≈$^4J_{H,H}$≈1.7 Hz; 7.65 d,d (CH, 1H) $^3J_{H,H}$≈$^4J_{H,H}$≈1.7 Hz; 4.33 t (CH$_2$, 2H), $J_{H,H}$=7.33 Hz; 4.03 s (CH$_3$, 3H); 1.92 m (CH$_2$, 2H); 1.40 m (CH$_2$, 2H); 0.94 t (CH$_3$, 3H), $J_{H,H}$=7.37 Hz.

$^{13}C\{^1H\}$-NMR (cation): δ, ppm=137.40 s (CH, 1C); 124.86 s (CH, 1C); 123.47 s (CH, 1C); 50.30 s (CH$_2$, 1C); 36.68 s (CH$_3$, 1C); 32.59 s (CH$_2$, 1C); 19.98 s(CH$_2$, 1C); 13.50 s (CH$_3$, 1C).

$^{11}$B-NMR: δ, ppm=−12.0 d, t (1B), $^1J_{F,B}$=51.6 Hz, $^2J_{F,B}$=25.2 Hz.

$^{19}$F-NMR: δ, ppm=−82.6 d, t (CF$_3$, 3F), $^3J_{F,F}$=1.0 Hz, $^4J_{F,F}$=6.3 Hz; −132.0 q,d (CF$_2$, 2F), $^3J_{F,F}$=5.0 Hz, $^2J_{F,B}$=25.3 Hz; −219.1 q, q, t (BF, 1F), $^1J_{F,B}$=52 Hz, $^3J_{F,F}$=5-6 Hz, $^4J_{F,F}$=5-6 Hz.

Elemental analysis. Found, %, C, 42.66; H, 4.39; N, 16.50; calculated for C$_{12}$H$_{15}$BF$_6$N$_4$, %, C, 42.38; H, 4.45; N, 16.47.

Example 31

1-Methoxyethyl-3-methylimidazolium dicyanofluoropentafluoroethylborate—[C$_7$H$_{13}$N$_2$O][C$_2$F$_5$BF(CN)$_2$]

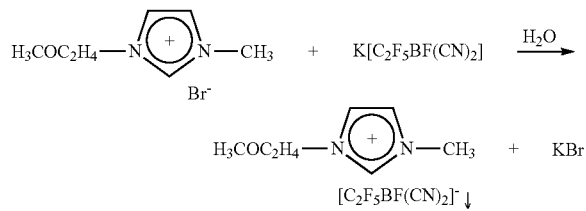

Potassium dicyanofluoropentafluoroethylborate K[C$_2$F$_5$BF(CN)$_2$] (5.1 g, 21.2 mmol), prepared as described in Example 6, and 1-methoxyethyl-3-methylimidazolium bromide [MOEMIM]Br (5.1 g, 23.0 mmol) are each dissolved in 2 ml of deionised water. The two solutions are combined, and the ionic liquid obtained is separated off and subsequently washed with deionised water (4×2 ml). The virtually colourless liquid obtained is dried at 60° C. in vacuo. The yield of 1-methoxyethyl-3-methylimidazolium dicyanofluoropentafluoroethylborate is 6.9 g (20.1 mmol), 95%, based on the potassium dicyanofluoropentafluoroethylborate K[C$_2$F$_5$BF(CN)$_2$] employed. The product is analysed by means of ion chromatography and has low levels of contamination with halide; bromide: <5 ppm, chloride: <5 ppm, fluoride: <5 ppm. Water content (Karl Fischer titration): 114 ppm.

Dynamic viscosity (20° C.): 25.5 mPa·s.

Raman spectroscopy: $\tilde{v}$ (CN)=2215 cm$^{-1}$ $^1$H-NMR: δ, ppm=8.94 d,d (CH, 1H), $^4J_{H,H}$≈1.7 Hz; 7.68 d,d (CH, 1H), $^3J_{H,H}$≈$^4J_{H,H}$≈1.7 Hz; 7.64 d,d (CH, 1H), $^3J_{H,H}$≈$^4J_{H,H}$≈1.7 Hz; 4.49 m (CH$_2$, 2H); 4.04 s (CH$_3$, 3H); 3.79 m (CH$_2$, 2H); 3.33 s (CH$_3$, 3H).

$^{13}$C{$^1$H}-NMR: δ, ppm=137.67 d (CH, 1C); 124.42 s (CH, 1C); 123.86 s (CH, 1C); 70.65 s (CH$_2$, 1C); 58.79 s (CH$_3$, 1C); 50.38 s (CH$_2$, 1C); 36.58 s (CH$_3$, 1C)

$^{11}$B-NMR: δ, ppm=−12.0 d, t (1B), $^1J_{F,B}$=51.6 Hz, $^2J_{F,B}$=25.2 Hz.

$^{19}$F-NMR: δ, ppm=−82.6 d, t (CF$_3$, 3F), $^3J_{F,F}$=1.0 Hz, $^4J_{F,F}$=6.3 Hz; −132.0 qd (CF$_2$, 2F), $^3J_{F,F}$=5.0 Hz, $^2J_{F,B}$=25.3 Hz; −219.1 q, q, t (BF, 1F), $^1J_{F,B}$=52 Hz, $^3J_{F,F}$=5-6 Hz, $^4J_{F,F}$=5-6 Hz.

Elemental analysis. Found, %, C, 38.86; H, 3.82; N, 16.43; calculated for C$_{11}$H$_{13}$BF$_6$ON$_4$, %, C, 38.63; H, 3.83; N, 16.38.

Example 32

Tetra-n-butylammonium dicyanofluoropentafluoroethylborate—[(n-C$_4$H$_9$)$_4$N][C$_2$F$_5$BF(CN)$_2$]

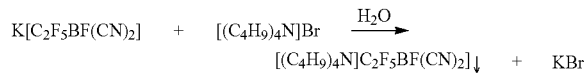

Potassium dicyanofluoropentafluoroethylborate, K[C$_2$F$_5$BF(CN)$_2$] (500 mg, 2.1 mmol), prepared as described in Example 6, is dissolved in deionised water (10 ml), and a solution of [n-Bu$_4$N]Br (0.8 g; 2.5 mmol) in deionised water (20 ml) is added. The fine precipitate formed is extracted with CH$_2$Cl$_2$ (2×30 ml). The combined organic phases are dried using MgSO$_4$, filtered, and the solvent is removed using a rotary evaporator. The yield of tetra-n-butylammonium dicyanofluoropentafluoroethylborate is 658 mg (1.5 mmol), 71%, based on the potassium dicyanofluoropentafluoroethylborate, K[C$_2$F$_5$BF(CN)$_2$], employed. Melting point: 52° C.

Raman spectroscopy: $\tilde{v}$ (CN)=2212 cm$^{-1}$.

$^1$H-NMR: δ, ppm=1.0 t (4CH$_3$, 12H), $^3J_{H,H}$=7 Hz; 1.4 m (4CH$_2$, 8H), $^3J_{H,H}$=7 Hz, 1.7-1.8 m (4CH$_2$, 8H); 3.3-3.5 m, (4CH$_2$, 8H).

$^{13}$C{$^1$H}-NMR (cation): δ, ppm=59.3 s (4C), 24.3 s (4C), 20.2 s (4C), 13.7 s(4C).

$^{11}$B-NMR: δ, ppm=−12.0 d, t (1B), $^1J_{F,B}$=51.6 Hz, $^2J_{F,B}$=25.2 Hz.

$^{19}$F-NMR: δ, ppm=−82.6 d, t (CF$_3$, 3F), $^3J_{F,F}$=1.0 Hz, $^4J_{F,F}$=6.3 Hz; −132.0 qd (CF$_2$, 2F), $^3J_{F,F}$=5.0 Hz, $^2J_{F,B}$=25.3 Hz; −219.1 q, q, t (BF, 1F), $^1J_{F,B}$=52 Hz, $^3J_{F,F}$=5-6 Hz, $^4J_{F,F}$=5-6 Hz.

Example 33

N-Butyl-N-methylpyrrolidinium dicyanofluoropentafluoroethylborate—[C$_9$H$_{20}$N][C$_2$F$_5$BF(CN)$_2$]

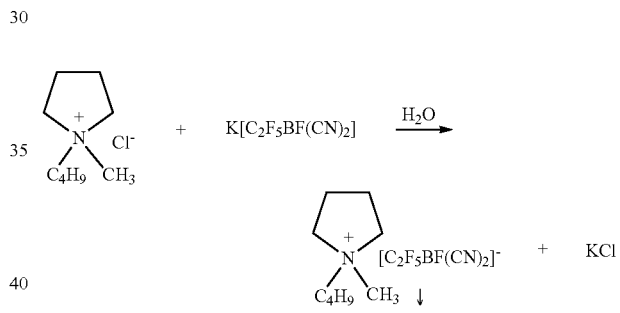

Potassium dicyanofluoropentafluoroethylborate K[C$_2$F$_5$BF(CN)$_2$] (5.0 g, 20.8 mmol), prepared as described in Example 6, and N-butyl-N-methylpyrrolidinium chloride [BMPL] (4.1 g, 23.0 mmol) are each dissolved in 2 ml of deionised water. The two solutions are combined, and the ionic liquid obtained is separated off and subsequently washed with deionised water (4×2 ml). The colourless liquid obtained is dried at 60° C. in vacuo. The yield of N-butyl-N-methylpyrrolidinium dicyanofluoropentafluoroethylborate is 6.6 g (19.2 mmol), 92%, based on the potassium dicyanofluoropentafluoroethylborate K[C$_2$F$_5$BF(CN)$_2$] employed. The product is analysed by means of ion chromatography and has low levels of contamination with halide; bromide: <5 ppm, chloride: 10 ppm, fluoride: <5 ppm. Water content (Karl Fischer titration): 191 ppm. Dynamic viscosity (20° C.): 38.5 mPa·s.

Raman spectroscopy: $\tilde{v}$ (CN)=2214 cm$^{-1}$ $^1$H-NMR: b=3.67 m (2CH$_2$, 4H); 3.50 m (CH$_2$, 2H); 2.82 s (CH$_3$, 3H), 2.30 m (2CH$_2$, 4H); 1.88 m (CH$_2$, 2H); 1.44 m (CH$_2$, 2H); 0.98 t (CH$_3$, 3H), $^3J_{H,H}$=7.37 Hz.

$^{13}$C{$^1$H}-NMR (cation): δ=65.20 s (2CH$_2$, 2C); 65.00 s (CH$_2$, 1C); 48.98 s (CH$_3$, 1C); 26.17 s (CH$_2$, 1C); 22.23 s (2CH$_2$, 2C); 20.30 s (CH$_2$, 1C); 13.64 s (CH$_3$, 1C).

$^{11}$B-NMR: δ, ppm=−12.0 d, t (1B), $^1J_{F,B}$=51.6 Hz, $^2J_{F,B}$=25.2 Hz.

$^{19}$F-NMR: δ, ppm=−82.6 dt (CF$_3$, 3F), $^3J_{F,F}$=1.0 Hz, $^4J_{F,F}$=6.3 Hz; −132.0 qd (CF$_2$, 2F), $^3J_{F,F}$=5.0 Hz, $^2J_{F,B}$=25.3 Hz; −219.1 q, q, t (BF, 1F), $^1J_{F,B}$=52 Hz, $^3J_{F,F}$=5-6 Hz, $^4J_{F,F}$=5-6 Hz.

Elemental analysis. Found, %, C, 45.86; H, 5.99; N, 12.27; calculated for C$_{13}$H$_{20}$BF$_6$N$_3$, %, C, 45.51; H, 5.88; N, 12.25.

Example 34

Tetraphenylphosphonium dicyanofluoropentafluorophenylborate—[(C$_6$H$_5$)$_4$P][C$_6$F$_5$BF(CN)$_2$]

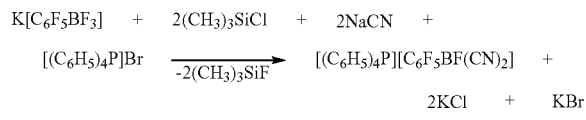

Dry sodium cyanide (12.5 g, 255.1 mmol) and sodium iodide (3.8 g, 25.1 mmol) are initially introduced in a 100 ml wide-necked flask with a stirrer bar and a reflux condenser. Acetonitrile (5 ml) and trimethylsilyl chloride (30 ml, 25.8 g, 237.5 mmol) are added in a counterstream of argon. After the suspension has been heated under reflux for 4 days, K[C$_6$F$_5$BF$_3$] (1.0 g, 3.6 mmol) is added, and the mixture is heated under reflux for a further 20 hours. All volatile constituents are subsequently condensed off in vacuo, and the trimethylsilyl cyanide formed (26.9 ml, 201.8 mmol) is purified by fractional distillation. The solid residue is dissolved in deionised water (10 ml) with addition of K$_2$CO$_3$. The aqueous phase obtained is extracted with THF (4×20 ml). The combined organic phases are dried using K$_2$CO$_3$ and evaporated to dryness in a rotary evaporator at 50° C. The residue is dissolved in deionised water (20 ml), and an aqueous [Ph$_4$P]Br solution (1.8 g, 4.3 mmol, 120 ml) is added dropwise. The suspension obtained is extracted with CH$_2$Cl$_2$ (3×20 ml). Impurities are precipitated by addition of Et$_2$O (50 ml) to the combined dichloromethane phases and are filtered off. The filtrate is concentrated slightly and stored at 8° C. for 4 days. The crystals formed are filtered and dried in vacuo. Yield: 0.6 g (1.1 mmol, 30%).

The product composition with respect to the borate anions was determined by $^{11}$B-NMR spectroscopy as [C$_6$F$_5$BF(CN)$_2$]$^-$ (80%), [C$_6$F$_5$B(CN)$_3$]$^-$ (16%) and an unknown species (4%).

$^1$H-NMR: δ, ppm=7.8-7.92 m (4C$_6$H$_5$, 16H); 7.97-8.05 m (4C$_6$H$_5$, 4H).

$^{13}$C{$^1$H}-NMR (cation): δ, ppm=136.3 s (4C), 135.6 d (8C), J$_{C,P}$=10 Hz, d (8C), J$_{C,P}$=13 Hz, 118.9 d (4C), J$_{C,P}$=91 Hz.

Example 35

1-Ethyl-3-methylimidazolium tricyanotrifluoromethylborate—[C$_6$H$_{11}$N$_2$][CF$_3$B(CN)$_3$]

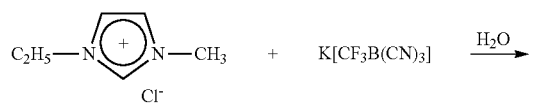

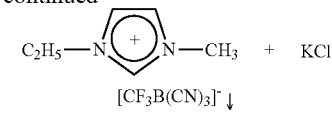

Potassium tricyanotrifluoromethylborate K[CF$_3$B(CN)$_3$] (96 mg, 0.48 mmol) is dissolved in deionised water (1 ml), and a solution of 1-ethyl-3-methylimidazolium chloride [EMIM]Cl (100 mg, 0.68 mmol) in 1 ml of deionised water is added. The aqueous phase is separated off, and ionic liquid obtained is washed with deionised water (2×2 ml), separated off and dried at 50° C. in vacuo. The yield of 1-ethyl-3-methylimidazolium tricyanotrifluoromethylborate is 98 mg (0.39 mmol). This corresponds the yield 75%, based on the potassium tricyanotrifluoromethylborate K[CF$_3$B(CN)$_3$] employed. The product is characterised by means of NMR spectroscopy.

$^1$H-NMR: δ, ppm=8.85 d,d (CH, 1H), $^4J_{H,H}$≈1.7 Hz; 7.79 d,d (CH, 1H), $^3J_{H,H}$≈$^4J_{H,H}$≈1.8 Hz; 7.66 d,d (CH, 1H) $^3J_{H,H}$≈$^4J_{H,H}$≈1.7 Hz; 4.42 t (CH$_2$, 2H), J$_{H,H}$=7.36 Hz; 4.07 s (CH$_3$, 3H); 1.57 t (CH$_3$, 3H), J$_{H,H}$=7.40 Hz.

$^{13}$C{$^1$H}-NMR (cation): δ, ppm=136.98 s (CH, 1C); 125.21 s (CH, 1C); 122.54 s (CH, 1C); 45.69 s (CH$_2$, 1C); 36.57 s (CH$_3$, 1C); 15.42 s (CH$_3$, 10).

$^{11}$B-NMR: δ, ppm=−32.0 q (1B), $^2J_{F,B}$=36.3 Hz.

$^{19}$F-NMR: δ, ppm=−66.4 q (CF$_3$, 3F), $^2J_{F,B}$=36.3 Hz.

Example 36

1-Ethyl-3-methylimidazolium tricyanopentafluoroethylborate—[C$_6$H$_{11}$N$_2$][C$_2$F$_5$B(CN)$_3$]

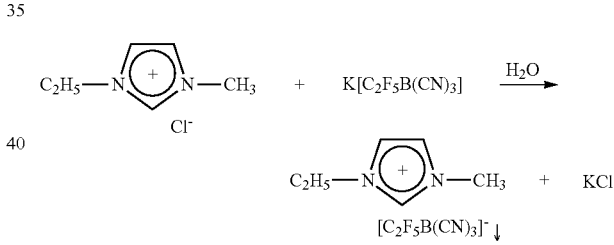

Potassium tricyanopentafluoroethylborate K[C$_2$F$_5$B(CN)$_3$] (160 mg, 0.64 mmol) is dissolved in deionised water (1 ml), and a solution of 1-ethyl-3-methylimidazolium chloride [EMIM]Cl (120 mg, 0.81 mmol) in 1 ml of deionised water is added. The aqueous phase is separated off, and ionic liquid obtained is washed with deionised water (2×2 ml), separated off and dried at 50° C. in vacuo. The yield of 1-ethyl-3-methylimidazolium tricyanopentafluoroethylborate is 180 mg (0.56 mmol). This corresponds the yield 87%, based on the potassium tricyanopentafluoroethylborate K[C$_2$F$_5$B(CN)$_3$] employed. The product is characterised by means of NMR spectroscopy.

$^1$H-NMR: δ, ppm=8.77 d,d (CH, 1H), $^4J_{H,H}$≈1.7 Hz; 7.71 d,d (CH, 1H), $^3J_{H,H}$≈$^4J_{H,H}$≈1.8 Hz; 7.62 d,d (CH, 1H) $^3J_{H,H}$≈$^4J_{H,H}$≈1.7 Hz; 4.37 t (CH$_2$, 2H), J$_{H,H}$=7.31 Hz; 4.02 s (CH$_3$, 3H); 1.50 t (CH$_3$, 3H), J$_{H,H}$=7.40 Hz.

$^{13}$C{$^1$H}-NMR (cation): δ, ppm=136.48 s (CH, 1C); 125.02 s (CH, 1C);
122.34 s (CH, 1C); 45.51 s (CH$_2$, 1C); 36.51 s (CH$_3$, 1C); 15.38 s (CH$_3$, 1C).

$^{11}$B-NMR: δ, ppm=−31.9 t (1B), $^2J_{F,B}$=25.2 Hz.

$^{19}$F-NMR: δ, ppm=−82.3 s (CF$_3$, 3F); −124.2 q (CF$_2$, 2F), $^2J_{F,B}$=25.2 Hz.

Example 37

Lithium cyanodifluoropentafluoroethylborate—Li[C$_2$F$_5$BF$_2$(CN)]

A solution of lithium tetrafluoroborate in acetonitrile (0.95 M, 4.52 ml, 4.29 mmol of LiBF$_4$) is added at room temperature to a solution of potassium cyanodifluoropentafluoroethylborate K[C$_2$F$_5$BF$_2$(CN)] (1.0 g, 4.29 mmol) in acetonitrile (3 ml). The suspension obtained is filtered at 0° C., and the precipitate (KBF$_4$) is rinsed with acetonitrile (0° C., 3 ml) and dried in vacuo. The filtrate is evaporated in vacuo, and the residue is dried at 50° C. in vacuo for 20 hours.

The yield of potassium tetrafluoroborate KBF$_4$ is 0.53 g (4.20 mmol, 98%). The yield of lithium cyanodifluoropentafluoroethylborate Li[C$_2$F$_5$BF$_2$(CN)] is quantitative. The product is characterised by means of NMR spectra.

$^{11}$B-NMR: δ, ppm=−2.7 tt (1B), $^1J_{F,B}$=51.0 Hz, $^2J_{F,B}$=25.3 Hz.

$^{19}$F-NMR: δ, ppm=−83.3 t (CF$_3$, 3F), $^4J_{F,F}$=5.2 Hz; −136.3 q (CF$_2$, 2F), $^2J_{F,B}$=23.3 Hz; −167.2 qq (BF$_2$, 2F), $^1J_{F,B}$=51.1 Hz, $^4J_{F,F}$=5.1 Hz.

Example 38

Potassium dicyanofluorophenylborate—K[C$_6$H$_5$BF(CN)$_2$]

K[C$_6$H$_5$BF$_3$] (0.5 g, 2.7 mmol) is suspended in trimethylsilyl cyanide, (10.0 ml, 74.9 mmol) and stirred at room temperature for 2 days. The slightly yellow solution obtained is evaporated to dryness and dissolved in acetone (3 ml). K[C$_6$H$_5$BF(CN)$_2$] is precipitated by addition of CHCl$_3$ (150 ml), filtered off and dried in vacuo.

Yield: 520 mg (2.62 mmol, 97%).

$^{11}$B-NMR (acetone-d$_6$): δ=−8.22 (d, $^1J(^{19}$F, $^{11}$B)=53.6 Hz, 1B) ppm.

$^{19}$F-NMR (acetone-d$_6$): δ=−206.06 (d, $^1J(^{19}$F, $^{11}$B) 54.6, 1F) ppm.

$^1$H-NMR (acetone-d$_6$): δ=7.51 (m, Ph, 2H), 7.18 (m, Ph, 2H), 7.11 (m, Ph, 1H) ppm. $^{13}$C{$^1$H}-NMR (acetone-d$_6$): δ=147.3 (m, BC$_{ph}$, 1C), 133.38 (m, CN, 2C), 132.00 (s, Ph, 2C), 127.65 (s, Ph, 2C), 126.77 (s, Ph, 1C) ppm.

IR (cm$^{-1}$): 3075, 3022, 2959, 2215, 1593, 1486, 1432, 1317, 1255, 1171, 1057, 1005, 997, 968, 925, 984, 871, 850, 755, 704, 654.

Raman (cm$^{-1}$): 3057, 2214, 1592, 1029, 996, 875, 655, 622.

The invention claimed is:

1. Process for the preparation of salts of the formula I $$M^{a+}[B(R_f)(CN)_x(F)_y]_a^-: \quad\quad I,$$

where
- $M^{a+}$ is a silver, magnesium, copper(I), copper(II), zinc(II), calcium cation, NH$_4^+$ or an organic cation,
- $R_f$ denotes a linear or branched perfluorinated alkyl group having 1 to 4 C atoms, C$_6$F$_5$, C$_6$H$_5$, partially fluorinated phenyl, or phenyl which is mono- or disubstituted by a perfluoroalkyl group having 1 to 4 C atoms, where the perfluoroalkyl group is selected independently of one another,
- a is 1 or 2,
- x is 1, 2 or 3,
- y is 0, 1 or 2 and
- x+y=3, by reaction of an alkali metal salt of the formula II $$Me^+[B(R_f)F_3]^- \quad\quad II,$$

where
- Me$^+$ is a lithium, potassium, sodium, caesium or rubidium salt and $R_f$ has a meaning indicated above with trialkylsilyl cyanide to give a salt of the formula III $$Me^+[B(R_f)(CN)_x(F)_y]^- \quad\quad III,$$

where Me$^+$, $R_f$, x and y have a meaning indicated above and the alkyl group of the trialkylsilyl cyanide is in each case, independently of one another, a linear or branched alkyl group having 1 to 4 C atoms, and by the subsequent salt-exchange reaction of the salts of the formula III with a salt of the formula IV, $$MA \quad\quad IV,$$

where
- M has a meaning indicated for $M^{a+}$ and
- A is selected from the group of the anions
  F$^-$, Cl$^-$, Br$^-$, I$^-$, OH$^-$, [HF$_2$]$^-$, [CN]$^-$, [SCN]$^-$, [R$_1$COO]$^-$, [R$_1$SO$_3$]$^-$, [R$_2$COO]$^-$, [R$_2$SO$_3$]$^-$, [R$_1$OSO$_3$]$^-$, [SiF$_6$]$^{2-}$, [BF$_4$]$^-$, [SO$_4$]$^{2-}$, [HSO$_4$]$^{1-}$, [NO$_3$]$^-$, [(R$_1$)$_2$P(O)O]$^-$, [R$_1$P(O)O$_2$]$^{2-}$, [(R$_1$O)$_2$P(O)O]$^-$, [(R$_1$O)P(O)O$_2$]$^{2-}$, [(R$_2$)$_2$P(O)]$^-$, [R$_2$P(O)O$_2$]$^{2-}$, tosylate, benzoate, oxalate, succinate, suberate, ascorbate, sorbate, tartrate, citrate, malate, malonate, malonates which are optionally substituted by alkyl groups having 1 to 4 C atoms, or [CO$_3$]$^{2-}$, where R$_1$ in each case, independently of one another, denotes H and/or a linear or branched alkyl group having 1 to 12 C atoms, R$_2$ in each case, independently of one another, denotes a partially fluorinated or perfluorinated linear or branched alkyl group having 1 to 12 C atoms or pentafluorophenyl and where electroneutrality must be ensured in the formula of the salt MA.

2. Process according to claim 1 for the preparation of salts of the formula I having anions of the formula Ia $$[B(R_f)(CN)(F)_2] \quad\quad Ia,$$

characterised in that the reaction of the compound of the formula II with the trialkylsilyl cyanide is carried out at temperatures between 10° C. and 110° C. or with microwave irradiation with 100 W.

3. Process according to claim 1 for the preparation of salts of the formula I having anions of the formula Ib $$[B(R_f)(CN)_2(F)] \quad\quad Ib,$$

characterised in that the reaction of the compound of the formula II with the trialkylsilyl cyanide is carried out at temperatures between 115 and 200° C. or with microwave irradiation with 200 W.

4. Process according to claim 1 for the preparation of salts of the formula I having anions of the formula Ic, $$[B(R_f)(CN)_3]^- \quad\quad Ic,$$

characterised in that the reaction of the compound of the formula II with the trialkylsilyl cyanide is carried out with microwave irradiation greater than 200 W.

5. Process according to claim 1, characterised in that the trialkylsilyl cyanide is prepared in situ from an alkali metal cyanide and a trialkylsilyl chloride in the presence of an alkali metal iodide and optionally iodine before the reaction with a compound of the formula II.

6. Process according to claim 1, characterised in that, after the reaction of the compound of the formula II with the trialkylsilyl cyanide, readily volatile by-products are separated off, but the compound of the formula III is reacted further without further purification with a compound of the formula IV.

7. Process according to claim 1, characterised in that compounds of the formula I are prepared in which the organic cation M' is selected from the group of the cations of the following formulae (1) to (8), $$[N(R)_4]^+ \quad (1),$$

$$[S(R)_3]^+ \quad (2)$$

or $[O(R)_3]^+ \quad (3)$ where
R in each case, independently of one another, denotes
H, where all substituents R cannot simultaneously be H,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or two R may be fully substituted and/or one or more R may be partially substituted by halogens or partially by —$OR^1$, —$NR^*{}_2$, —CN, —$C(O)NR^1{}_2$ or —$SO_2NR^1{}_2$,
and where one or two non-adjacent carbon atoms which are not in the α-position of the radical R may be replaced by atoms and/or atom groups selected from the group —O—, —S—, —S(O)—, —$SO_2$—, —$N^+R^1{}_2$—, —$C(O)NR^1$—, —$SO_2NR^1$— or —$P(O)R^1$—; or $$[P(R^2)_4]^+ \quad (4),$$

where
$R^2$ in each case, independently of one another, denotes
H, $NR^{1*}{}_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or two $R^2$ may be fully substituted and/or one or more $R^2$ may be partially substituted by halogens, or partially by —$OR^1$, —CN, —$C(O)NR^1{}_2$, —$SO_2NR^1{}_2$,
and where one or two non-adjacent carbon atoms which are not in the α-position of the $R^2$ may be replaced by atoms and/or atom groups selected from the group —O—, —S—, —S(O)—, —$SO_2$—, —$N^+R^1{}_2$—, —$C(O)NR^1$—, —$SO_2NR^1$—, or —$P(O)R^1$—; or $$[C(NR^3R^4)(OR^5)(NR^6R^7)]^+ \quad (5)$$

or $$[C(NR^3R^4)(SR^5)(NR^6R^7)]^+ \quad (6),$$

where
$R^3$ to $R^7$ each, independently of one another, denote
H, $NR^{1*}{}_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents $R^3$ to $R^7$ may be partially or fully substituted by halogens, or partially by —OH, —$OR^1$, —CN, —$C(O)NR^1{}_2$, —$SO_2NR^1{}_2$,
and where one or two non-adjacent carbon atoms which are not in the α-position of $R^3$ to $R^7$ may be replaced by atoms and/or atom groups selected from the group —O—, —S—, —S(O)—, —$SO_2$—, —$N^+R^1{}_2$—, —$C(O)NR^1$—, —$SO_2NR^1$—, or —$P(O)R^1$—; or $$[C(NR^8R^9)(NR^{10}R^{11})(NR^{12}R^{13})]^+ \quad (7),$$

where
$R^8$ to $R^{13}$ each, independently of one another, denote
H, $NR^{1*}{}_2$,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents $R^8$ to $R^{13}$ may be partially or fully substituted by halogens or partially by —$OR^1$, —CN, —$C(O)NR^1{}_2$, —$SO_2NR^1{}_2$,
and where one or two non-adjacent carbon atoms which are not in the α-position of $R^8$ to $R^{13}$ may be replaced by atoms and/or atom groups selected from the group —O—, —S—, —S(O)—, —$SO_2$—, —$N^+R^1{}_2$—, —$C(O)NR^1$—, —$SO_2NR^1$—, or —$P(O)R^1$—; or $$[HetN]^+ \quad (8),$$

where $[HetN]^+$ is a heterocyclic cation, selected from the group comprising

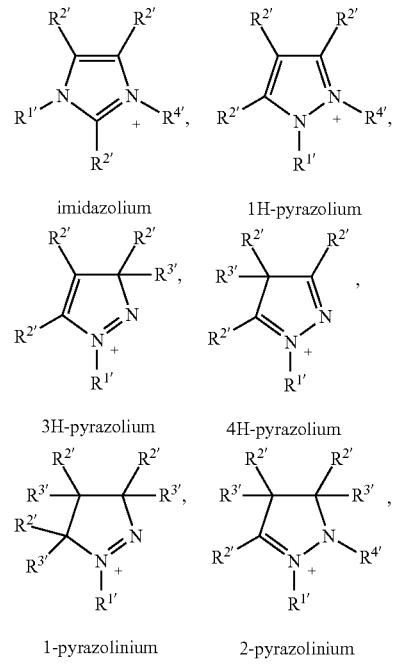

-continued
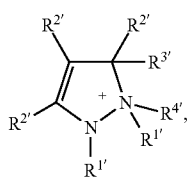
3-pyrazolinium
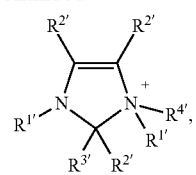
2,3-dihydroimidazolinium
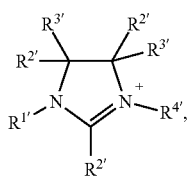
4,5-dihydroimidazolinium
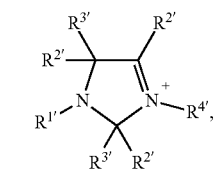
2,5-dihydroimidazolinium
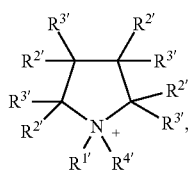
pyrrolidinium
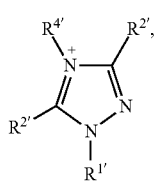
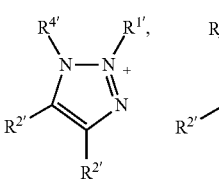
1,2,4-triazolium
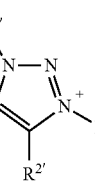
1,2,4-triazolium    1,2,3-triazolium    1,2,3-triazolium
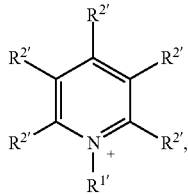
pyridinium
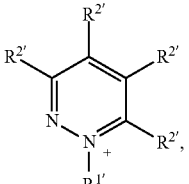
pyridazinium
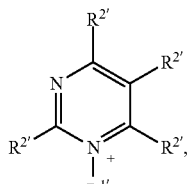
pyrimidinium
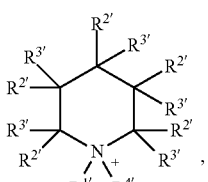
piperidinium
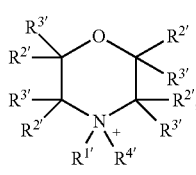
morpholinium
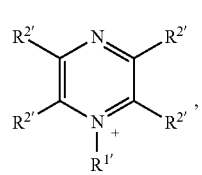
pyrazinium
-continued
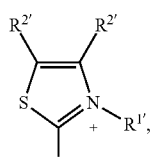
thiazolium
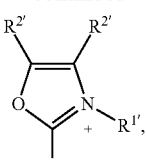
oxazolium
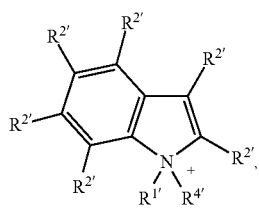
indolium
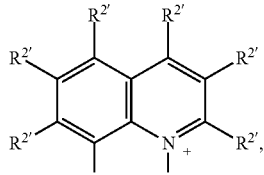
quinolinium
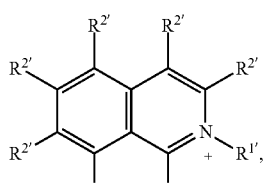
isoquinolinium
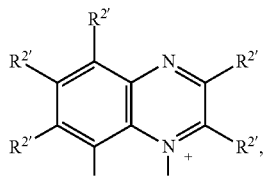
quinoxalinium
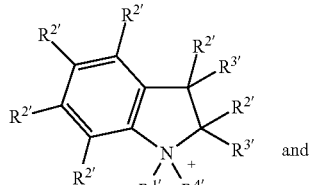
and
indolinium

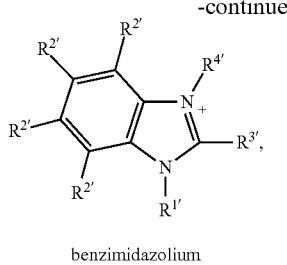

benzimidazolium where the substituents $R^{1'}$ to $R^{4'}$ each, independently of one another, denote H, with the restriction that $R^{1'}$ and $R^{4'}$ cannot simultaneously be H, straight-chain or branched alkyl having 1-20 C atoms, which may be fluorinated or perfluorinated, straight-chain or branched alkenyl having 2-20 C atoms and one or more double bonds, which may also be fluorinated or perfluorinated, straight-chain or branched alkynyl having 2-20 C atoms and one or more triple bonds, which may also be fluorinated or perfluorinated, saturated, partially or fully unsaturated cycloalkyl having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may form a ring system, where one or more substituents $R^{1'}$ to $R^{4'}$ may be partially or fully substituted by halogens or partially by —$OR^1$, —CN, —C(O)$NR^1_2$, —$SO_2NR^1_2$, but where $R^{1'}$ and $R^{4'}$ cannot simultaneously be fully substituted by halogens, and where one or two non-adjacent carbon atoms which are not bonded to the heteroatom of the substituents $R^{1'}$ to $R^{4'}$ may be replaced by atoms and/or atom groups selected from the group —O—, —S—, —S(O)—, —$SO_2$—, —$N^+R^1_2$—, —C(O)$NR^1$—, —$SO_2NR^1$—, or —P(O)$R^1$—;

in which $R^1$ stands for H, non-, partially or perfluorinated $C_1$- to $C_6$-alkyl, $C_3$- to $C_7$-cycloalkyl, unsubstituted or substituted phenyl and $R^{1*}$ stands for non-, partially or perfluorinated $C_1$- to $C_6$-alkyl, $C_3$- to $C_7$-cycloalkyl, unsubstituted or substituted phenyl.

8. Process for the preparation of compounds of the formula III $$Me^+[B(R_f)(CN)_x(F)_y]^- \qquad III,$$

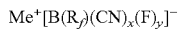

where $Me^+$ is a lithium, potassium, sodium, caesium or rubidium salt, $R_f$ denotes a linear or branched perfluorinated alkyl group having 1 to 4 C atoms, $C_6F_5$, $C_6H_5$, partially fluorinated phenyl, or phenyl which is mono- or disubstituted by a perfluoroalkyl group having 1 to 4 C atoms, where the perfluoroalkyl group is selected independently of one another, x is 1, 2 or 3, y is 0, 1 or 2 and x+y is 3, by reaction of an alkali metal salt of the formula II $$Me^+[B(R_f)F_3]^- \qquad II,$$

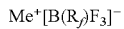

where $Me^+$ and $R_f$ have an above-mentioned meaning, with a trialkylsilyl cyanide, where the alkyl group of the trialkylsilyl cyanide is in each case, independently of one another, a linear or branched alkyl group having 1 to 4 C atoms.

9. Process according to claim 8, characterised in that the reaction for the preparation of compounds of the formula III where x=1, y=2 is carried out at temperatures between 10° C. and 110° C. or with microwave irradiation of 100 W, in that the reaction for the preparation of compounds of the formula III where x=2 and y=1 is carried out at temperatures between 115 and 200° C. or with microwave irradiation of 200 W or in that the reaction for the preparation of compounds of the formula III where x=3 and y=0 is carried out with microwave irradiation of greater than 200 W.

\* \* \* \* \*

UNITED STATES PATENT AND TRADEMARK OFFICE
CERTIFICATE OF CORRECTION

PATENT NO. : 8,927,757 B2  
APPLICATION NO. : 13/522526  
DATED : January 6, 2015  
INVENTOR(S) : Nikolai Mykola Ignatyev Page 1 of 1

It is certified that error appears in the above-identified patent and that said Letters Patent is hereby corrected as shown below:

In the Claims

Column 50, Line 24 reads: "$[(R_2)_2P(O)]^-$, $[R_2P(O)O_2]^{2-}$, tosylate, benzoate," should read -- $[(R_2)_2P(O)O]^-$, $[R_2P(O)O_2]^{2-}$, tosylate, benzoate, --

Column 51, Line 6 reads: "cation M' is selected from the group of the cations of the" should read -- cation $M^{a+}$ is selected from the group of the cations of the --

Column 51, Line 26 reads: "partially by $-OR^1$, $-NR^{*1}_2$, -CN, $-C(O)NR^1_2$ or," should read -- partially by $-OR^1$, $-NR^{1*}_2$, -CN, $-C(O)NR^1_2$ or --

Signed and Sealed this  
Eleventh Day of August, 2015

Michelle K. Lee  
*Director of the United States Patent and Trademark Office*